United States Patent
Li et al.

(10) Patent No.: US 8,647,636 B2
(45) Date of Patent: *Feb. 11, 2014

(54) LOW ANTIGEN-DOSE IMMUNIZATION UTILIZING OVERLAPPING PEPTIDES FOR MAXIMIZING T-HELPER CELL 1 (TH1) IMMUNITY AGAINST A PATHOGEN

(75) Inventors: Yihang Li, Lansing, MI (US); Erfan Ullah Chowdhury, Auburn, AL (US); Bernhard Kaltenboeck, Auburn, AL (US)

(73) Assignee: Auburn University, Auburn, AL (US)

( * ) Notice: Subject to any disclaimer, the term of this patent is extended or adjusted under 35 U.S.C. 154(b) by 9 days.

This patent is subject to a terminal disclaimer.

(21) Appl. No.: 13/602,833

(22) Filed: Sep. 4, 2012

(65) Prior Publication Data

US 2012/0328644 A1    Dec. 27, 2012

Related U.S. Application Data

(63) Continuation of application No. 12/949,559, filed on Nov. 18, 2010.

(60) Provisional application No. 61/262,216, filed on Nov. 18, 2009.

(51) Int. Cl.
*A61K 39/40*    (2006.01)
*A61K 39/395*    (2006.01)
*A61K 51/00*    (2006.01)
*A61M 36/14*    (2006.01)

(52) U.S. Cl.
USPC ..... 424/203.1; 424/1.49; 424/1.57; 424/1.69; 424/130.1; 424/139.1; 424/150.1; 424/178.1; 424/184.1; 424/234.1; 424/263.1

(58) Field of Classification Search
None
See application file for complete search history.

(56) References Cited

U.S. PATENT DOCUMENTS

| | | | | |
|---|---|---|---|---|
| 6,166,177 A * | 12/2000 | Probst et al. | | 530/300 |
| 6,372,223 B1 | 4/2002 | Kistner et al. | | |
| 7,252,937 B2 | 8/2007 | Kaltenboeck | | |
| 7,811,592 B2 | 10/2010 | Johnston et al. | | |
| 2002/0183272 A1 * | 12/2002 | Johnston et al. | | 514/44 |
| 2003/0185848 A1 | 10/2003 | Johnston et al. | | |

(Continued)

FOREIGN PATENT DOCUMENTS

| | | |
|---|---|---|
| EP | 1618890 | 1/2006 |
| WO | 2008025095 | 3/2008 |

OTHER PUBLICATIONS

Ghilzai et al., "Pulmonary Drug Delivery".

(Continued)

*Primary Examiner* — Ja'na Hines
(74) *Attorney, Agent, or Firm* — Andrus Intellectual Property Law, LLP

(57) ABSTRACT

Disclosed are compositions, kits, and methods for inducing an immune response against disease. The dosage of antigen contained or utilized in the presently disclosed compositions, kits, and methods is substantially lower than dosages conventionally used in the field. The compositions, kits, and methods may be utilized to induce a cell-mediated response, such as a T-helper cell response, and/or a humoral response against a pathogen or a disease. In some embodiments, the compositions, kits, and methods may be utilized to induce preferentially a Th1 response versus other types of immune responses such as a Th2 response.

20 Claims, 11 Drawing Sheets

(56) References Cited

U.S. PATENT DOCUMENTS

| | | | |
|---|---|---|---|
| 2005/0202048 | A1 | 9/2005 | Murdin et al. |
| 2007/0149474 | A1 | 6/2007 | Johnston et al. |
| 2008/0025998 | A1 | 1/2008 | Johnston et al. |
| 2008/0160027 | A1 | 7/2008 | Sykes et al. |

OTHER PUBLICATIONS

Office Action for U.S. Appl. No. 12/949,559, dated Sep. 14, 2012.
Bergmann et al., "Th1 or Th2: How an Approriate T Helper Response can be Made", Bulletin of Mathematical Biology, 2001, 63:405-430.
Bergmann et al., "How Instruction and Feedback Can Select the Appropriate T Helper Response", Bulletin of Mathematical Biology, 2002, 64:425-446.
Biesenkamp-Uhe et al., "Therapeutic *Chlamydophila abortus* and *C. pecorum* Vaccination Transiently Reduces Bovine Mastitis Associated with *Chlamydophila* Infection", Infection and Immunity, Feb. 2007, 75(2):870-877.
Bryan et al., "Low-Dose Intradermal and Intramuscular Vaccination against Hepatitis B", Clinical Infectious Diseases, Mar. 1992, 14(3):697-707.
Coiter et al., "Dissemination of *Chlamydia trachomatis* Chronic Genital Tract Infection in Gamma Interferon Gene Knockout Mice", Infection and Immunity, Jun. 1997, 65(6):2145-2152.
Evans et al., "QS-21 promotes an adjuvant effect allowing for reduced antigen dose during HIV-1 envelope subunit immunization in humans", Vaccine, 2001, 19:2080-2091.
Jiang et al., "Overlappng synthetic peptides as vaccines", Vaccine, 2006, 24:6356-6365.
Kenney et al., "Dose Sparing with Intradermal Injection of Influenza Vaccine", New England Journal of Medicine, 2004, 351:2295-2301.
Li et al., "Novel *Chlamydia pneumoniae* vaccine candidates confirmed by Th1-enhanced genetic immunization", Vaccine, Feb. 10, 2010, 28(6):1598-1617.
Lu et al.. "*Chlamydia trachomatis* Mouse Pneumonitis Lung Infection in IL-18 for Protective Immunity". Molecular Medicine, 2000, 6(7):604-612.
Morrison et al., "Gene Knockout Mice Establish a Primary Protective Role for Major Histocompatibility Complex Class II-Restricted Responses in *Chlamydia trachomatic* Genital Tract Infection", Infection and Immunity, Dec. 1995,63(12):4661-4668.
Perry et al., "Immunity to *Chlamydia trachomatis* is Mediated by T Helper 1 Cells Through IFN-•-Dependent and—Independent Pathways", The Journal of Immunology, 1997, 158:3344-3352.
Rodenberg et al., "Regulation and Role of IFN-γ in the Innate Resistance to Infection with *Chlamydia pneumoniae*", J Immunol, 2000,164:4812-4818.
Scheifele et al., "Safety and Immunogenicity of a Pentavalent Combination Vaccine (Diphtheria, Tetanus, Acellular Pertussis, Polio, and Haemophilus Influenzae Type b Conjugate) when Administered as a Fourth Dose at 15 to 18 Months of Age", Human Vaccines, Sep./Oct. 2005,1(5):180-186.
Stemke-Hale et al., "Screening the whole genome of a pathogen in vivo for individual protective antigens", Vaccine, 2005, 23:3016-3025.
Vuola et al., "Acquired Immunity to *Chlamydia pneumoniae* Is Dependent on Gamma Interferon in Two Mouse Strains That Initially Differ in This Respect after Primary Challenge", Infection and Immunity, Feb. 2000, 68 (2):960-964.
Wang et al., "IFN-• knockout mice show Th2-associated delayed-type hypersensitivity and the inflammatory cells fail to localize and control chlamydial infection", Eur. J. Immunol., 1999, 29:3782-3792.
Zhang et al., "Comparing Pooled Peptides with Intact Protein for Accessing Cross-presentation Pathways for Protective CD8+ and CD4+ T Cell", Journal of Biological Chemistry, Apr. 3, 2009, 284(14):9184-9191.
International Search Report and Written Opinion dated Feb. 25, 2011, for PCT/US2010/057250.
International Preliminary Report on Patentability for PCT/US2010/057250 dated May 31, 2012.

\* cited by examiner

FIG. 4

Chlamydia abortus / 100 mg lung (Log$_{10}$)

- Naive
- Live-vaccine *
- 0.002% Polygen®
- 0.02% Polygen®
- 0.2% Polygen®
- 2% Polygen®

FIG. 6

```
  1 mtsatyqvss rkyrpqtfae mlgqdavvtv iknalqfqrv ahaylfsgir gtqkttlari
 61 fakalnckel tpehepcnqc cvckeissgt slqvieidga shrqiedirq inetvliftpa
121 ksqykiylid evhmltkeaf nsliktleep pshvkfflat tenykipsti lsrcqkmhlk
181 ripetmivdk lasisqaggi etsreallpi araaggeird aeslydyvig lfptslspel
241 vadalqllsq dtlatlseci rtqkyaeall pvttainsgv apitfihdlt vfyrdvlink
301 dqgnsplsai amhyssecll eilldflgeaa khlqgtlfek tfletvlihl lricqrpsle
361 tllfsqlktst fdtvrnvpqq qepskpsigp ekhyqdqsfii tspsptpkvq hqkeaspslv
421 gsatidtllq favvefsgll tke
```

LOW ANTIGEN-DOSE IMMUNIZATION UTILIZING OVERLAPPING PEPTIDES FOR MAXIMIZING T-HELPER CELL 1 (TH1) IMMUNITY AGAINST A PATHOGEN

CROSS-REFERENCE TO RELATED APPLICATIONS

This application is a continuation application of U.S. patent application Ser. No. 12/949,559, which application claims the benefit under 35 U.S.C. §119(e) to U.S. Provisional Application No. 61/262,216, filed on Nov. 18, 2009, the content of which is incorporated herein by reference in its entirety.

BACKGROUND

The present invention relates generally to the field of compositions, kits, and methods for inducing an immune response against a disease. In particular, the invention relates to compositions, kits, and methods for administering a relatively low dose of antigen for inducing an immune response against a disease as compared to conventional compositions, kits, and methods.

T-helper (Th) lymphocytes may be categorized into two distinct subsets of effector cells based on their functional capabilities and cytokine profiles. Th1 cells produce IFN-γ, TNF-β, and IL-2 and help to activate macrophages and cytotoxic T lymphocytes. In addition, Th1 cells assist other immune cells in the production of those antibody isotypes that promote opsonization. Th2 cells trigger B cells to produce and secrete antibodies. In contrast, Th2 cells are particularly effective at inducing B cells to produce certain antibody isotypes such as IgE and IgA, which neutralize intercellular pathogens and help opsonization, complement, mast cell, and eosinophil activation. Because of these functional differences, Th1 and Th2 exhibit different efficiency in elimination of a selected pathogen. Diseases that can be prevented or treated successfully by Th1 responses include mycobacterial infections such as tuberculosis, leprosy, leishmaniasis, and schistosomiasis, which are intracellular infections, and certain viral diseases. Th2 responses are protective against helminths and some bacteria such as pneumo- and meningococcii.

Th1 and Th2 cells arise from a common precursor cell called Th0. Differentiation of T-helper cells into Th1 and Th2 cells is an important event in determining the outcome of an immune response (i.e., whether a pathogen will persist, whether the host will be protected, and/or whether the host will experience immunopathogenesis). Infectious pathogens may exhibit a predisposition to induce a cell-mediated form of immunity versus a humoral form of immunity. Successful defense against intracellular pathogens tends to be associated with Th1 dominance and resultant cellular cytolytic activity, whereas resistance to extracellular infectious pathogens is most often dominated by Th2 effectors, which lead to the production of high levels of antigen-specific immunoglobulins. Therefore, a better understanding of the factors that contribute to differentiation of Th0 cells into Th1 and Th2 cells will help facilitate preparation of more effective prevention and treatment strategies.

SUMMARY

Disclosed are compositions, kits, and methods for inducing an immune response against a disease. The composition, kits, and methods contain or utilize a protein, polypeptide, peptide, or panel thereof as an antigen. The dosage of antigen contained or utilized in the presently disclosed compositions, kits, and methods is substantially lower than that dosage conventionally used in the field (e.g., by at least an order of magnitude (10x)). The compositions, kits, and methods may be utilized to induce a cell-mediated response (e.g., a T-helper cell response) and/or a humoral response against a disease. In some embodiments, the compositions, kits, and methods may be utilized to induce preferentially a Th1 response versus other types of immune responses (e.g., a Th2 response).

The compositions, kits, and methods include or utilize a relatively low amount of antigen compared to vaccines and methods of the art. As contemplated herein, suitable doses administered to a subject in need thereof may be no more than about 2 pg antigen/g body weight (preferably no more than about 1 pg antigen/g body weight, more preferably no more than about 0.5 pg antigen/g body weight, more preferably no more than about 0.2 pg antigen/g body weight, more preferably no more than about 0.1 pg antigen/g body weight, more preferably no more than about 0.05 pg antigen/g body weight, even more preferably no more than about 0.01 pg antigen/g body weight). In some embodiments, a suitable dose administered to a subject in need thereof may be at least about 0.01 pg antigen/g body weight, at least about 0.05 pg antigen/g body weight, or at least about 0.1 pg antigen/g body weight. For example, suitable dose ranges may include 0.01-0.05 pg antigen/g body weight, 0.01-0.1 pg antigen/g body weight, or 0.01-0.2 pg antigen/g body weight, 0.01-1 pg antigen/g body weight, 0.01-2 pg antigen/g body weight, 0.05-0.1 pg antigen/g body weight, 0.05-0.2 pg antigen/g body weight, 0.05-1 pg antigen/g body weight, or 0.05-2 pg antigen/g body weight, 0.1-0.2 pg antigen/g body weight, 0.1-1 pg antigen/g body weight, or 0.1-2 pg antigen/g body weight.

The compositions, kits, and methods disclosed herein may involve administering a peptide or a panel of peptides as an antigen in order to induce an immune response against a disease. For example, the compositions, kits, and methods disclosed herein may involve administering a peptide or a panel of peptides comprising 5-100 amino acids (preferably 10-20 amino acids). Typically, the peptides have a molecular weight of no more than about 5 kDa (preferably no more than about 4 kDa, more preferably no more than about 3 kDa). Suitable doses of the peptide or the panel of peptides administered to a subject in need thereof as described by moles administered per gram body weight of subject may be no more than about 1 femtomole each peptide/g body weight (preferably no more than about 0.5 femtomoles each peptide/g body weight, more preferably no more than about 0.1 femtomoles each peptide/g body weight, more preferably no more than about 0.05 femtomoles each peptide/g body weight, even more preferably no more than about 0.01 femtomoles each peptide/g body weight). In some embodiments, a suitable dose administered to a subject in need thereof as described by moles each peptide per gram body weight of subject may be at least about 0.01 femtomoles each peptide/g body weight, or at least about 0.05 femtomoles antigen/g body weight. For example, suitable dose ranges may include 0.01-0.05 femtomoles antigen/g body weight, 0.01-0.1 femtomoles antigen/g body weight, 0.01-0.5 femtomoles antigen/g body weight, include 0.01-1 femtomoles antigen/5.1 body weight 0.05-0.1 femtomoles antigen/body weight 0.05-0.5 femtomoles antigen/g body weight, and 0.05-1 femtomoles antigen/g body weight.

The presently disclosed compositions, which may include pharmaceutical compositions such as vaccines, typically include a lower concentration of antigen as compared to compositions in conventional use. Vaccines that comprise an antigen solution typically have an antigen concentration of no more than about $1.5 \times 10^{-6}$ g antigen/ml (preferably no more than about $1.5 \times 10^{-7}$ g antigen/ml, more preferably no more than about $1.5 \times 10^{-8}$ g antigen/ml, more preferably no more than $1.5 \times 10^{-9}$ g antigen/ml, even more preferably no more than about $1.5 \times 10^{-10}$ g antigen/ml). In some embodiments, the vaccines comprise an antigen solution having an antigen concentration of at least about $1.5 \times 10^{-10}$ g antigen/ml. For example, suitable concentration ranges may include $1.5 \times 10^{-10}$-$3 \times 10^{-10}$ g antigen/ml, $1.5 \times 10^{-10}$-$6 \times 10^{-10}$ g antigen/ml, $1.5 \times 10^{-10}$-$1.5 \times 10^{-9}$ g antigen/ml, $1.5 \times 10^{-10}$-$3 \times 10^{-9}$ g antigen/ml, or $1.5 \times 10^{-10}$-$6 \times 10^{-9}$ g antigen/ml.

The vaccines disclosed herein may comprise a peptide or a panel of peptides as an antigen. For example, the vaccines may comprise a peptide or a panel of peptides comprising 5-100 amino acids (preferably 10-20 amino acids). Typically, the peptides have a molecular weight of no more than about 5 kDa (preferably no more than about 4 kDa, more preferably no more than about 3 kDa). Vaccines that comprise a peptide or a panel of peptides in solution typically have a solution concentration of each peptide of no more than about $7.5 \times 10^{-10}$ moles each peptide/ml (preferably no more than about $1.5 \times 10^{-11}$ moles each peptide/ml, more preferably no more than about $7.5 \times 10^{-12}$ moles each peptide/ml, more preferably no more than about $1.5 \times 10^{12}$ moles each peptide/ml, more preferably no more than about $7.5 \times 10^{-13}$ moles each peptide/ml, even more preferably no more than about $1.5 \times 10^{-13}$ moles each peptide/ml). In some embodiments, the vaccines comprise a peptide solution having a concentration of at least about $1.5 \times 10^{-13}$ moles each peptide/ml, or at least about $1.5 \times 10^{-13}$ moles each peptide/ml. For example, suitable concentration ranges may include $1.5 \times 10^{-13}$-$3 \times 10^{-13}$ moles each peptide/ml, $1.5 \times 10^{-13}$-$6 \times 10^{-13}$ moles each peptide/ml, $1.5 \times 10^{-13}$-$1.5 \times 10^{-12}$ moles each peptide/ml, $1.5 \times 10^{-13}$-$6 \times 10^{-13}$ moles each peptide/ml, $3 \times 10^{-13}$-$6 \times 10^{-13}$ moles each peptide/ml, $3 \times 10^{-13}$-$1.5 \times 10^{-12}$ moles each peptide/ml, $3 \times 10^{-13}$-$3 \times 10^{-12}$ moles each peptide/ml.

Kits contemplated herein include kits for preparing vaccine compositions. For example, a contemplated kit ma include a lyophilized antigen and a pharmaceutical solution comprising a carrier, diluent, excipient, or adjuvant for combining with the lyophilized antigen to prepare the vaccine. Typically, the kits comprise no more than about $1.5 \times 10^{-7}$ g total lyophilized antigen (preferably no more than about $7.5 \times 10^{-8}$ g total lyophilized antigen, more preferably no more than about 1.5 g total lyophilized antigen, more preferably no more than about $7.5 \times 10^{-9}$ g total lyophilized antigen, preferably no more than about $7.5 \times 10^{-9}$ g total lyophilized antigen, even more preferably no more than about $7.5 \times 10^{-10}$ g total lyophilized antigen) for mixing with 0.1-5 mls of a pharmaceutical solution. When the lyophilized antigen is combined with the pharmaceutical solution, an antigen solution is provided typically having an antigen concentration of no more than about $1.5 \times 10^{-6}$ g antigen ml (preferably no more than about $1.5 \times 10^{-7}$ g antigen/ml, more preferably no more than about $1.5 \times 10^{-8}$ g antigen/ml, more preferably no more than $1.5 \times 10^{-9}$ g antigen/ml, even more preferably no more than about $1.5 \times 10^{-10}$ g antigen ml). For example, a suitable kit may contain $7.5 \times 10^{-10}$-$1.5 \times 10^{-7}$ g total lyophilized antigen and 0.1-5 mls of a pharmaceutical solution comprising a carrier, diluent, excipient, or adjuvant for combining with the antigen to prepare a vaccine.

The kits disclosed herein may comprise a lyophilized peptide or a panel of peptides as an antigen. For example, the kits may comprise a lyophilized peptide or a panel of peptides comprising 5-100 amino acids (preferably 10-20 amino acids). A panel of peptides may be present in the kit as a mixture. Typically, the peptides have a molecular weight of no more than about 5 kDa (preferably no more than about 4 kDa, more preferably no more than about 3 kDa). Typically, the kits comprise no more than about $7.5 \times 10^{-11}$ moles each peptide (preferably no more than about $1.5 \times 10^{-11}$ moles each peptide, more preferably no more than about $7.5 \times 10^{-12}$ moles each peptide, more preferably than about $1.5 \times 10^{-12}$ each peptide, even more preferably no more than about $7.5 \times 10^{-13}$ moles each peptide) for mixing with 0.1-5 mls of a pharmaceutical solution. When the lyophilized peptide or panel of peptides are combined with the pharmaceutical solution, an solution is provided typically having concentration of no more than about $7.5 \times 10^{-10}$ moles each peptide/ml (preferably no more than about $1.5 \times 10^{-11}$ motes each peptide/ml, more preferably no more than about $7.5 \times 10^{-12}$ moles each peptide/ml, more preferably no more than about $1.5 \times 10^{-12}$ moles each peptide/ml, more preferably no more than about $7.5 \times 10^{-13}$ moles each peptide/ml, even more preferably no more than about $1.5 \times 10^{-13}$ moles each peptide/ml). For example, a suitable kit may contain $7.5 \times 10^{-13}$-$7.5 \times 10^{-11}$ moles each peptide and 0.1-5 mls of a pharmaceutical solution comprising a carrier, diluent, excipient, or adjuvant for combining with the antigen to prepare a vaccine.

Suitable antigens may include polypeptides, peptides, or panels thereof that comprise one or more epitopes of a protein associated with a disease. For example suitable polypeptides, peptides, or panels thereof may comprise one or more epitopes of a protein associated with a pathogen. Suitable polypeptides may comprise the lull-length amino acid sequence of a corresponding protein of a pathogen or a fragment thereof. For example, suitable fragments may include 5-200 amino acids (or from 5-150, 5-100, 5-50, 5-25, 5-15, 10-200, 10-100, 10-50, 10-25, 10-25, or 10-15 amino acids) and include at least one epitope of the protein from which the fragment is derived. Suitable antigens for the compositions, kits, and methods may include panels of peptides derived from a protein of a pathogen. For example, a suitable antigen may comprise a panel of at least 2, 3, 4, 5, 10, 25, 50, 100, or more different peptides comprising at least about a 10-20 amino acid sequence from a protein of a pathogen. The different peptide antigens may overlap at the N-terminus, the C-terminus, or both termini with at least one other peptide antigen of the composition, for example, by at least about 1, 2, 3, 4, 5, 6, 7, 8, 9, or 10 amino acids.

The compositions disclosed herein may include pharmaceutical compositions such as vaccines. Typically, the pharmaceutical composition comprises an effective amount or concentration of the antigen for inducing a protective or therapeutic immune response against a disease, which may include, but is not limited to infection by a pathogen, cancer, or an autoimmune disease. Inducing a protective or therapeutic immune response may include inducing a Th1 response to one or more epitopes of a protein associated with the disease (e.g., a protein associated with a pathogen, cancer, or autoimmune disease).

Where the disease relates to infection by a pathogen, inducing a protective response may include inducing sterilizing immunity against the pathogen. Inducing a therapeutic response may include reducing the pathogenic load of a subject, for example, as determined by measuring the amount of circulating pathogen before and after administering the composition. Inducing a therapeutic response may include reducing the degree or severity of at least one symptom of infection by the pathogen.

The presently disclosed methods flay be utilized for inducing a protective or therapeutic immune response against disease by administering the pharmaceutical compositions disclosed herein (e.g., as immunogenic compositions or vaccines) to a subject in need thereof, which may include a human or non-human having or at risk for acquiring the disease. The methods may include administering a first pharmaceutical composition and optionally may include administering a second pharmaceutical composition to augment or boost an immunogenic response induced by the first pharmaceutical composition. The first and second pharmaceutical compositions may be the same or different. The optionally administered second pharmaceutical composition may be administered prior to, concurrently with, or after administering the first pharmaceutical composition. In some embodiments, the first composition is administered and then the second composition is administered after waiting at least about 4, 5, or 6 weeks. The first composition (and the second composition) may be administered one or more times.

Also disclosed are kits that may include the pharmaceutical compositions disclosed herein or kits that may be used to prepare and administer the pharmaceutical compositions disclosed herein. For example, the kits may include an individual antigen or a panel of antigens for inducing an immune response against a disease (e.g., infection by pathogen, cancer, or autoimmune disease). The kits may be used to practice the methods disclosed herein and may include as components: the pharmaceutical compositions disclosed herein, additional therapeutic or prophylactic agents, pharmaceutical solutions (e.g., pharmaceutical solutions comprising carriers, diluents, excipients, or adjuvants), implements, and/or instructions for combining the kit components to prepare a vaccine and/or administer the vaccine.

Figure 1:
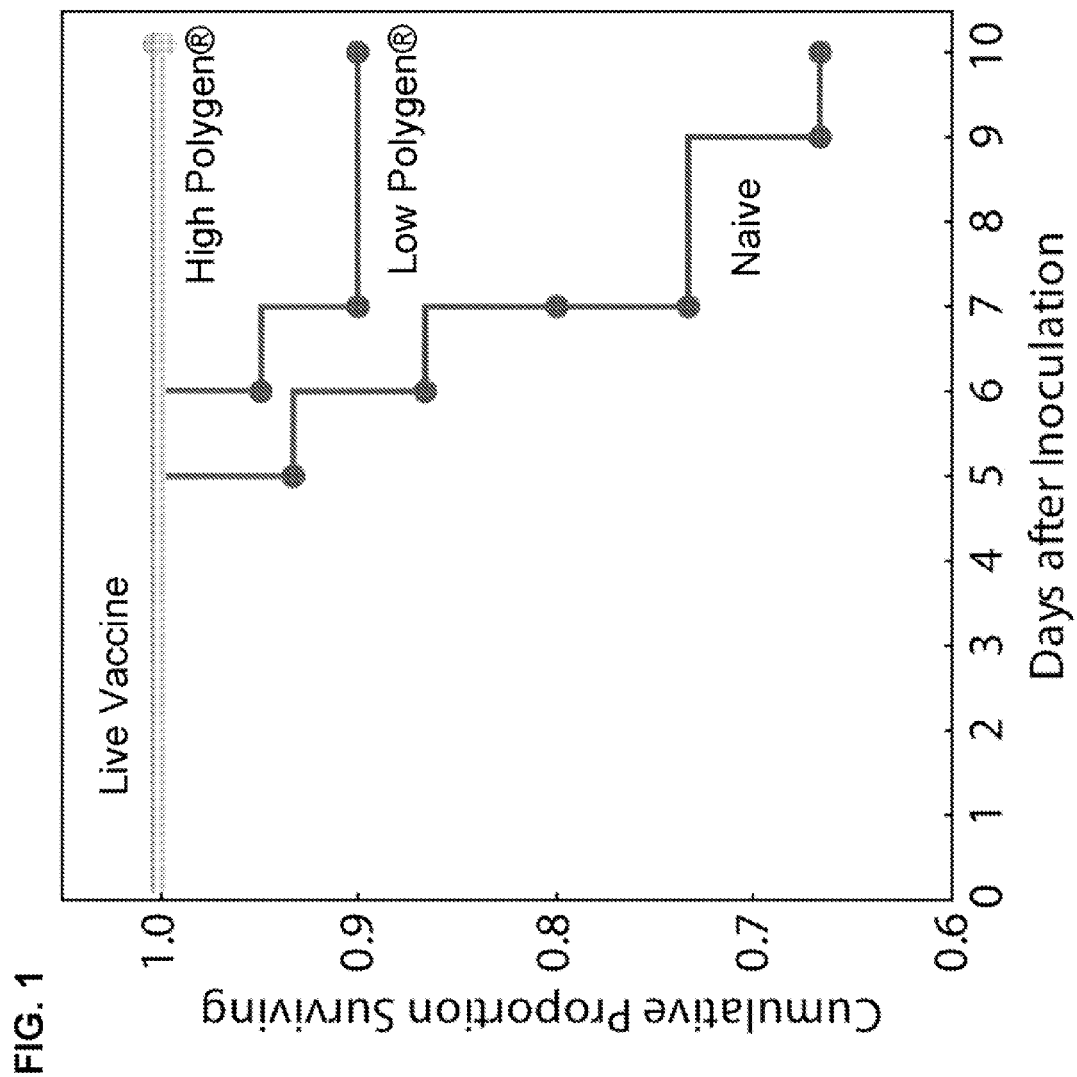
FIG. 1. Protection from lethal disease by low antigen-dose vaccination. Survival of mice is shown in a Kaplan-Meier plot. Live-vaccine indicates mice that received a low-dose ($10^6$ genomes) intranasal *C. abortus* inoculum 4 weeks prior to the high-dose ($10^8$ genomes) challenge infection and that are fully protected against *C. abortus*-induced disease. The designation "low Polygen®" indicates pooled groups with 0.002% or 0.02% Polygen® adjuvant. The designation "high Polygen®" indicates pooled groups with 0.2% or 2.0% Polygen® adjuvant. Naïve (mock vaccinated) mice have significantly lower survival rates than all other treatment groups ($p \leq 0.04$; Cox's F and Cox-Mantel tests). The other treatment groups do not differ significantly from each other.

FIG. 2. Post inoculation body weight loss (≈disease) after vaccination. Body weight losses in the 0.002%, 0.02%, and 2% Polygen® adjuvant groups are increasingly lower than in the naïve controls, but not significantly so. The live-vaccine controls have significantly lower body weight loss than the naïve controls ($p=0.005$; Fisher LSD test). Significant differences to the naïve mice are indicated by an asterisk.

FIG. 3. Post inoculation lung weight increase (≈disease) after vaccination. Lung weight increases in the live-vaccine, 0.002%, and 2% Polygon® adjuvant groups are significantly lower than in the naïve controls ($p \leq 0.03$; Fisher LSD test).

FIG. 4. Post inoculation *C. abortus* lung concentration after vaccination. Naive A/J mice have highly significantly higher *C. abortus* lung loads than live-vaccine mice ($p<0.001$; Fisher LSD test). Polygen® adjuvant groups have lower chlamydial lung loads (except for the 0.2% Group) than naïve mice, but the difference is not statistically different. All Polygen® adjuvant groups have significantly higher chlamydial lung loads than live-vaccine mice ($p \leq 0.04$).

FIG. 5. Disease Susceptibility Score after vaccination. Polygen® adjuvant groups (except for the 0.2% outlier) and live-vaccine controls have significantly lower disease susceptibility than naïve mice ($p \leq 0.026$; Fisher LSD test). All Poly adjuvant groups also show significantly higher disease susceptibility than live-vaccine mice ($p \leq 0.042$). Because of the trend for lower susceptibility at increasing adjuvant doses, and the lowest susceptibility of the 2% Polygen® adjuvant vaccine group, the 2% Polygen® adjuvant concentration was considered optimal for vaccination and used in further experiments.

FIG. 6. Graphic illustration of use of overlapping peptides (20-mers overlapping by 10 amino acids) of a full-length peptide to create an antigen panel. Shown is the sequence of DNA polymerase III subunit gamma/tau [*Chlamydophila abortus* S26/3].

FIG. 7. Post inoculation body weight loss (≈disease) after vaccination. Body weight losses in all vaccine groups are very low and do not differ from the live-vaccine controls. This conforms with the observation that no mouse showed signs of disease or died prior to sacrificing on day 10. The absolute body weight loss of these groups is very similar to the live-vaccine controls of Example 1, as shown in the left panel for comparison.

FIG. 8. Post inoculation lung weight increase (≈disease) after vaccination. Lung weight increases in all vaccine groups were low and did not differ significantly from the live-vaccine control. Again, lung weight increases in Example 2 are in the range of the lung weight increase of the live-vaccine controls in Example 1.

FIG. 9. Post inoculation *C. abortus* lung concentration after vaccination. The 1 ng doses of proteins and peptides in the Polygen® adjuvant vaccine have significantly higher chlamydial lung loads than live-vaccine mice ($p<0.048$ Fisher LSD test). None of the other vaccine groups differ significantly from live-vaccine control. Again, chlamydial lung loads are in the range of the lung loads of the live-vaccine and the 2% Polygen® adjuvant vaccine in Example 1.

FIG. 10. Dissection of factor effects on post inoculation *C. abortus* lung concentration after vaccination. Left panel: Chlamydial lung loads do not differ significantly between Polygen® adjuvant and Poly (I:C) vaccines. Right panel: Decreasing peptide doses show a trends towards decreasing chlamydial lung loads, and the load at the lowest peptide dose of 0.1 ng is significantly lower than that of the vaccine with 1 ng of each protein ($p=0006$; Fisher LSD test).

FIG. 11. Disease Susceptibility Score after vaccination. Disease susceptibility calibrated against disease susceptibility of naïve and live-vaccine controls in Example 1 is very low in all vaccine groups and does not differ from the live-vaccine controls. This conforms with the observation that no mouse showed signs of disease or died prior to sacrificing on day 10. The data indicate that protein vaccines mediate less than 100% protection relative to the live-vaccine controls in Example 2. In contrast, peptide vaccines, particularly combined with Poly (I:C) adjuvant at 1, 0.5, and 0.1 ng peptide doses mediate essentially 100% protection.

DETAILED DESCRIPTION

Disclosed herein are compositions, kits, and methods for inducing an immune response against disease which may be described using several definitions as discussed below.

Unless otherwise specified or indicated by context, the terms "a", "an", and "the" mean "one or more." in addition, singular nouns such as "antigen" should be interpreted to mean "one or more antigens," unless otherwise specified or indicated by context.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising."

A "subject," "patient," or "host" refers to a human or non-human having, or at risk for acquiring infection a disease that is amenable to treatment or protection by a vaccine. Individuals who are treated with the pharmaceutical compositions disclosed herein may be at risk for infection with a pathogen or may have already been infected with the pathogen. Individuals who are treated with the pharmaceutical compositions disclosed herein may be at risk for cancer or may have already acquired cancer. Individuals who are treated with the pharmaceutical compositions disclosed herein may be at risk for autoimmune disease or may have already acquired autoimmune disease.

The terms "subject," "patient," or "host" may be used interchangeably. Non-human hosts may include, but are not limited to, cows, pigs, horses, dogs, and cats.

A "panel" or "plurality" or antigens as used herein means "more than one" and may mean more than 1, 2, 3, 4, 5, 10, 25, 50, or 100 antigens. A panel or plurality of antigens may include a set of different, overlapping polypeptides (e.g., polypeptides of about 10-20 amino acids that overlap by about 5-10 amino acids) where the overlapping polypeptides correspond to a full-length polypeptide associated with a disease. A panel of polynucleotides may encode different or unique amino acid sequences of a selected polypeptide. The encoded different or unique amino acid sequences may overlap. For example, a panel of overlapping polypeptides may correspond to the full-length sequence of a protein where a first polypeptide of a panel includes amino acids 1-20 of the protein, the second polypeptide of the panel includes amino acids 11-30 of the protein, the third polypeptide of the panel includes amino acids 21-40 of the protein, the fourth polypeptide of the panel includes amino acids 31-50 of the protein, such the overlapping polypeptides of the panel encompass all of the amino acid sequence of the protein.

The presently disclosed compositions, kits, and methods may be utilized to protect against or treat infection by a pathogen. As used herein, a "pathogen" includes, but is not limited to a living microorganism such as bacteria, viruses, and fungi that cause disease in a host. Suitable pathogens for treatment of prevention by the compositions, kits, and methods disclosed herein may include pathogens that are susceptible to cell-mediated immune responses in the host (e.g., Th1-mediated immune response) such as *Chlamydia* spp. (e.g. *Chlamydia abortus, Chlamydia trachomatis, Chlamydia suis, Chlamydia muridarum, Chlamydophila pneumoniae, Chlamydophila pecorum, Chlamydophila psittaci, Chlamydophila abortus, Chlamydophila felis*, and *Chlamydophila caviae*). The presently disclosed compositions, kits, and methods also may be utilized to protect against or treat cancers or hyperproliferative disorders that are susceptible to cell-mediated immune responses in the host (e.g., Th1-mediated immune response), which may include, but are not limited to adenocarcinoma, leukemia, lymphoma, melanoma, myeloma, sarcoma, and teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus. The presently disclosed compositions, kits, and methods also may be utilized to protect against or treat autoimmune diseases that are susceptible to cell-mediated immune responses in the host (e.g., Th1-mediated immune response), which may include, but are not limited to autoimmune haematological disorders (including e.g. hemolytic anaemia, aplastic anaemia, pure red cell anaemia and idiopathic thrombocytopenia), systemic lupus erythematosus, polychondritis, sclerodoma, Wegener granulomatosis, chronic active hepatitis, myasthenia gravis, psoriasis, Steven-Johnson syndrome, idiopathic sprue, autoimmune inflammatory bowel disease (including e.g. ulcerative colitis, Crohn's disease and Irritable Bowel Syndrome), endocrine Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis or glomerulonephritis (with and without nephrotic syndrome, e.g. including idiopathic nephrotic syndrome or minimal change nephropathy).

The compositions, kits, and methods include or utilize a relatively low amount of antigen to induce an immune response a Th-1 response) compared to convention vaccines and methods of the art. Conventional vaccines and methods typically involve administering at least about 3 μg of an antigen per dose to a subject. See, e.g., Scheifele et al. 2005, Hum. Vaccin. 1:180-186; Evans et al. 2001, Vaccine 19:2080-2091; and Kenney et al., N. Engl. J. Med. 351:2295-2301, the contents of which are incorporated herein by reference in their entireties). However, a dose as low as 1 μg of an antigen per dose to a subject also has been proposed. (See U.S. Pat. No. 6,372,223, the content of which is incorporated herein by reference in its entirety). Assuming that the subject is human and weighs approximately 75 kg, a dose of 1 μg antigen translates to a dose of 13.3 pg antigen/g body weight. Surprisingly, the present inventors have found that a dose rate that is an order of magnitude lower (e.g., no more than about 2 pg antigen/g body weight) can be administered in order to induce an immune response (e.g., a Th1-response). For peptide vaccines, the present inventor have found that a dose rate of 1 femtomole each peptide/g body weight or lower can be administered in order to induce an immune response (e.g., a Th1-response).

As used herein, "potentiating" or "enhancing" an immune response means increasing the in and/or the breadth of the immune response. For example, the number of cells that recognize a particular epitope may be increased ("magnitude") and/or the numbers of epitopes that are recognized may be increased. ("breadth"). Preferably, a 5-fold, or more preferably a 10-fold or greater, enhancement in T-cell responses may be obtained by administering the pharmaceutical composition disclosed herein.

The presently disclosed compositions, kits, and methods may be utilized to induce an immune response, including, but not limited to a cellular immune response such as a "Th1-response." As utilized herein, a Th1-response may be characterized by cytokine production such as interferons (e.g., IFN-γ), tumor necrosis factor (e.g., TNF-β), and interleukins (e.g., IL-2). A Th1-response also may be characterized by increased killing efficiency of macrophages with respect to a pathogen and the proliferation of cytotoxic $CD8^+$ cells against the pathogen. A Th1 response also may be characterized by the presence of opsonizing antibodies against the antigen. Th1-responses may be assessed as described previously. (See Li et al, Vaccine 28 (2010) 1598-1605, the content of which is incorporated herein by reference in its entirety).

In some embodiments, the presently disclosed COM positions, kits, and methods may be utilized to induce a Th1-response preferentially relative to other responses, for example, a Th2-response. As utilized herein, a Th2-response may be characterized by cytokine production such as interleukins (e.g., IL-4, IL-5, IL-6, IL-10, and IL-13). A Th2-response also may be characterized by B-cell stimulation and proliferation to induce B-cell antibody class switching and to increase neutralizing antibody production. Computer models have suggested that a Th1-response versus a Th2-response may be dependent on antigen dosage, (See Bergmann et al., Bulletin of Math. Biol. (2002) 64, 425-446; and Bergmann et al., Bulletin of Math. Biol. (2001) 63, 405-439, the contents of which are incorporated by reference in their entireties).

The presently disclosed composition, kits, and methods may be utilized to prevent or treat infections by pathogens that are susceptible to a I-cell mediated immune response (e.g., a Th1 immune response). In some embodiments, the presently disclosed composition, kits, and methods may be utilized to prevent or treat infections by *Chlamydia* spp. As is the case for many other intracellular pathogens, T-lymphocytes play a key role in a protective host response to *CHlamydia* infection (Morrison et al., 1995, Infect. Immun. 63.4661-4668; Rank, 2006, *In Chlamydia* Genomics and Pathogenesis. P. M. Bavoil and B. Wyrick (ed.). Horizon Bioscience Press, Norfolk, U. K.). IFN-γ producing Th1 helper lymphocytes are indispensible for efficient and complete elimination of chlamydial infection (Perry et at, 1997, J. Immunol, 158:3344-3352, Rottenberg et al., 2000, J. Immunol. 164:4812-4818; Vuola et al., 2000. Infect. Immun 68:960-964), and ablation of Th1 cells or effector functions results in increased chlamydial disease and failure to eliminate chlamydiae (Cotter et al., 1997, Infect. Immun. 65:2145-2152; Lu et al., 2000, Mol. Med. 6:604-612; Morrison et al., 1995, Infect. Immun. 63:4661-4668; Wang et al., 1999, Eur. J. Immunol. 29:3782-3792.) They restrict chlamydial replication via Th1-type effector cytokines, most prominently IFN-γ, contributing to a DTH response (Perry et al., 1997; Rottenberg et al., 2000). Such protective DTH responses are characterized by tissue infiltration of CD-4$^+$ T cells and macrophages and release of proinflammatory Th1 cytokines such as IL-1, IL-2, IL-12, IFN-γ, or TNF-α.

The presently disclosed compositions, kits, and methods contain and/or utilize a protein, polypeptide, or peptide for inducing an immune response. The presently disclosed compositions, kits, and methods are distinguished from live vaccines or inactivated vaccines in that the protein, polypeptide, or peptide of the compositions, kits, and methods is isolated, purified, recombinant, or synthesized in vitro (e.g., chemically synthesized). For example, the compositions, kits, and methods contain and/or utilize a protein, polypeptide, or peptide that is recombinant, expressed in a host cell, and isolated or purified. In another example, the compositions, kits, and methods may contain a panel of polypeptides or peptides that are chemically synthesized (e.g., using liquid phase synthesis, or solid phase synthesis such as Fmoc solid phase synthesis or t-hoc solid phase synthesis).

As utilized herein, a protein, polypeptide, and peptide refer to a molecule comprising a chain of amino acid residues joined by amide linkages. The term "amino acid residue," includes but is not limited to amino acid residues contained in the group consisting of alanine (Ala or A), cysteine (Cys or C) aspartic acid (Asp or D), glutamic acid (Glu or E), phenylalanine (Phe or F), glycine (Gly or G), histidine (His or H), isoleucine (Ile or I), lysine (Lys or K) leucine (Leu or L), methionine (Met or M), asparagine (Asn or N) proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine.

The terms "protein," "polypeptide," and "peptide" may be referred to interchangeably herein. However, the terms may be distinguished as follows. A "protein" typically refers to the end product of transcription, translation, and post-translation modifications in a cell. Accordingly, a protein typically exhibits a biological function. A polypeptide is typically an amino acid chain of length≥100 amino acids (Garrett & Grisham, Biochemistry, 2$^{nd}$ edition, 1999, Brooks/Cole, 110, which is incorporated herein by reference in its entirety). A polypeptide, as contemplated herein, may comprise, but is not limited to 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues. A peptide, in contrast to a polypeptide, typically is a short polymer of amino acids, of a length typically of 20 or less amino acids (Garrett & Grisham, Biochemistry, 2$^{nd}$ edition, 1999, Brooks/Cole, 110, which is incorporated herein by reference in its entirety). In some embodiments, a peptide as contemplated herein may include no more than about 10, 11, 12, 13, 14, 15, 16, 17, 18, 19, or 20 amino acids.

Polypeptides and peptides as contemplated herein may be further modified to include non-amino acid moieties. Modifications may include but, are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenyl prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein), polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, many to serine, tyrosine, threonine or histidine).

A "fragment" of a protein or a poly peptide as contemplated herein refers to a contiguous portion of the amino acid sequence of the protein or polypeptide. A fragment of a protein or polypeptide refers to less than a full-length amino acid sequence of the protein or polypeptide (e.g., where the full-length amino acid sequence is truncated at the N-terminus, the C-terminus, or both termini). For example, a fragment of a protein or polypeptide may comprise or consist of a 5-200, 5-150, 5-100, 5-50, 5-25, 5-15, 10-200, 10-150, 10-100, 10-50, 10-25, or 10-15 contiguous amino acid sequence of the full-length protein or polypeptide. An "immunogenic fragment" of a protein or polypeptide is a fragment of a protein or polypeptide typically at least 5 or 10 amino acids in length that includes one or more epitopes of the full-length protein or polypeptide (e.g., a peptide present in the full-length protein or polypeptide).

Formulation of the Pharmaceutical Compositions

The pharmaceutical compositions disclosed herein may be formulated as vaccines for administration to a subject in need thereof. Such compositions can be formulated and/or administered in dosages and by techniques well known to those skilled in the medical arts taking into consideration such factors as the age, sex, weight, and condition of the particular patient, and the route of administration. The compositions may include pharmaceutical solutions comprising carriers, diluents, excipients, or adjuvants as known in the art. Further, the compositions may include preservatives (e.g., anti-microbial or anti-bacterial agents such as benzalkonium chloride) or adjuvants.

The pharmaceutical compositions may be administered prophylactically or therapeutically. In prophylactic administration, the vaccines may be administered in an amount sufficient to induce a cellular immune response for protecting against infection or for treating infection in therapeutic applications, the vaccines are administered to a patient in an amount sufficient to elicit a therapeutic effect (e.g., an immune response to the administered antigen, which cures or at least partially arrests or slows symptoms and/or complications of disease (i.e., a "therapeutically effective dose.")).

In some embodiments, the pharmaceutical COM positions (e.g., comprising an antigen in an aqueous solution) may be injected into tissue (e.g., intramuscularly, intradermally, or subcutaneously), in amounts of from 10 µl per site to about 1 ml per site. The antigen may be delivered in a physiologically compatible solution such as sterile PBS. The pharmaceutical composition can also be lyophilized prior to delivery and reconstituted prior to administration.

The compositions included in the vaccine regimen of the invention can be co administered or sequentially administered with other immunological, antigenic or vaccine or therapeutic compositions, including an adjuvant, a chemical or biological agent given in combination with an antigen to enhance immunogenicity of the antigen. Additional therapeutic agents may include, but are not limited to, cytokines such as interferons (e.g., IFN-γ) and interleukins (e.g., IL-2).

The pharmaceutical composition disclosed herein may be delivered via a variety of routes. However, typical delivery routes involve parenteral administration (e.g., intradermal, intramuscular or subcutaneous delivery).

Adjuvants

The term "adjuvant" refers to a compound or mixture that enhances the immune response to an antigen. An adjuvant can serve as a tissue depot that slowly releases the antigen and also as a lymphoid system activator that non-specifically enhances the immune response. Examples of adjuvants which may be employed include but are not limited to, co-polymer adjuvants (e.g. CRL1005 or a low molecular weight co-polymer adjuvant such as Polygen® adjuvant), poly (I:C), R-848 (a Th1-like adjuvant), imiquimod, PAM3CYS, aluminum phosphates (e.g. $AlPO_4$), loxoribine, potentially useful human adjuvants such as BCG (Bacille Calmette-Guerin) and *Corynebacterium parvum*, CpG oligodeoxynucleotides (ODN), cholera toxin derived antigens (e.g., CTA1-DD), lipopolysaccharide adjuvants, complete Freund's adjuvant, incomplete Freund's adjuvant, saponin (e.g., Quil-A), mineral gels such as aluminum hydroxide, surface active substances such as lysolecithin, pluronic polyols, polyanions, peptides, oil or hydrocarbon emulsions in water (e.g., MF59 available from Novartis Vaccines or Montanide ISA 720), keyhole limpet heinocyanins, and dinitrophenol.

Prime-Boost Vaccination Regimen

As used herein, a "prime-boost vaccination regimen" refers to a regimen in which a subject is administered a first composition and then after a determined period of time (e.g., after about 4, 5, or 6 weeks), the subject is administered a second composition, which may be the same or different than the first composition. The first composition (and the second composition) may be administered one or more times. For example, the first composition may include a first peptide vaccine and the second composition may include a second peptide vaccine. The disclosed methods may include priming a subject with a first peptide vaccine by administering the first peptide vaccine at least one time allowing a predetermined length of time to pass (e.g., at least about 4, 5, or 6 weeks), and then boosting by administering another peptide vaccine, which may be the same or different than the first vaccine.

Characterization of the Immune Response in Vaccinated Individuals

The pharmaceutical compositions disclosed herein may be delivered to subjects at risk for a disease (e.g., infection with a pathogen) or to subjects who have acquired the disease (e.g., subject who are infected with a pathogen). In order to assess the efficacy of the vaccine, the immune response can be assessed by measuring the induction of cell-mediated responses and/or antibodies to particular epitopes. T-cell responses may be measured, for example, by using tetramer staining of fresh or cultured PBMC, ELISPOT assays or by using, functional cytotoxicity assays, which are well-known to those of skill in the art. Antibody responses may be measured by assays known in the art such as ELLSA. Titer or load of a pathogen may be measured using methods in the art including methods that detect nucleic acid of the pathogen. (See, e.g., U.S. Pat. No. 7,252,937, the content of which is incorporated by reference in its entirety). Immune responses also may be characterized by physiological responses. (See Li et al., Vaccine 28 (2010) 1598-1605; and Stemke-Hale et al., Vaccine 2005 Apr. 27; 23(23):3016-25, the content of which are incorporated herein by reference in their entireties.)

EXAMPLES

The following examples are illustrative and are not intended to limit the disclosed subject matter.

Example 1

Low Dose Antigen Administration and Titration of Adjuvant

In this Example, 1 ng each of *Chlamydophila abortus* vaccine candidate proteins DnaX2, GatA, and GatC, were combined with Polygen® adjuvant in a *C. abortus* respiratory challenge model. Challenge models have been described previously. (See U.S. Publication No. 2004/0071634). DnaX2, GatA, and GatC of *Chlamydia* spp. have been described previously. (See Stemke-Hale et al., Vaccine 2005 Apr. 27; 23(243016-25; U.S. Pat. Nos. 7,811,592; and U.S. Publication Nos. U.S. 2008/0160027; 2008/0025998; 2007/0149474; and 2003/0185848; the content of which are incorporated by reference in their entireties).

As shown in Table 1, all tested vaccines contained 1 nanogram of each the three recombinant *C. abortus* vaccine candidate proteins (DnaX2. GatA, and GatC) and comprised Polygen® adjuvant in the indicated volume/volume percentage (0.002%; 0.02%; 0.2%; or 2%) in 200 µl Hank's Balanced Salt Solution (HBSS).

TABLE 1

| GROUP | # of female A/J mice | Vaccine | Adjuvant | Week 0 antigen | Week 4 antigen | Week 8 |
|---|---|---|---|---|---|---|
| 1 *C. abortus* naive control | 15 | HBSS | HBSS | HBSS | HBSS | *C. abortus* challenge |
| 2 *C. abortus* live-vaccine control | 15 | low-dose infection | — | HBSS | low-dose intranasal *C. abortus* | *C. abortus* challenge |
| 3 titer Polygen ® adjuvant | 10 | protein | Polygen ® 0.002% | 1 ng sc | 1 ng sc | *C. abortus* challenge |
| 4 titer Polygen ® adjuvant | 10 | protein | Polygen ® 0.02% | 1 ng sc | 1 ng sc | *C. abortus* challenge |
| 5 titer Polygen ® adjuvant | 10 | protein | Polygen ® 0.2% | 1 ng sc | 1 ng sc | *C. abortus* challenge |
| 6 titer Polygen ® adjuvant | 10 | protein | Polygen ® 2% | 1 ng sc | 1 ng sc | *C. abortus* challenge |

Mice received the vaccines twice under light isoflurane inhalation anesthesia by subcutaneous injection between the shoulders in a 4-week interval at 6 weeks and 10 weeks of age. All mice (A/J inbred mouse strain, female, 14-weeks old) were challenged 4 weeks after the second vaccination under light isoflurane anesthesia intranasally with $10^8$ *C. abortus* bacteria (genomes) suspended in 20 µl sucrose-phosphate-glutamate buffer. After 10 days, the mice were sacrificed and lungs were homogenized, DNA was extracted, and *C. abortus* genome lung loads were determined by a FRET real-time PCR targeting the *Chlamydia* spp. 23S rRNA gene.

Naïve, mock-vaccinated mice served as controls for a complete lack of protective immunity against *C. abortus*. These mice developed maximum disease and eliminated chlamydiae less efficiently than immunoprotected mice.

Mice that received a low intranasal dose of $10^6$ *C. abortus* bacteria (genomes) 4 weeks before the high-dose challenge infection served a controls for protective immunity. Results for survival of mice were analyzed by the Kaplan-Meier Product-Limit Method, and for group effects by one-way ANOVA.

For mice that died before sacrificing on day 10, body weight losses, lung weight increases and chlamydial lung loads of the mouse in any group were taken as the highest of each of these parameters prior to death for the day 10 values. Next a disease susceptibility score was determined. The disease susceptibility score is an approximation of the Wei-Lachin method to enhance statistical power of the analysis of multiple outcomes with similar trends in the same animals. Data for lung weight increase, body weight loss, and *C. abortus* lung concentration were separately normalized to have equal weight (set to mean=0 and SD=1), and subsequently pooled. This composite score with 3-fold numbers of observations provided increased statistical power and allowed overall evaluation of disease protection mediated by vaccination. Data are shown as least-square means±SEM. All animal experiments were approved by the Auburn University Institutional Animal Care and Use Committee (IACUC).

Figure 2:
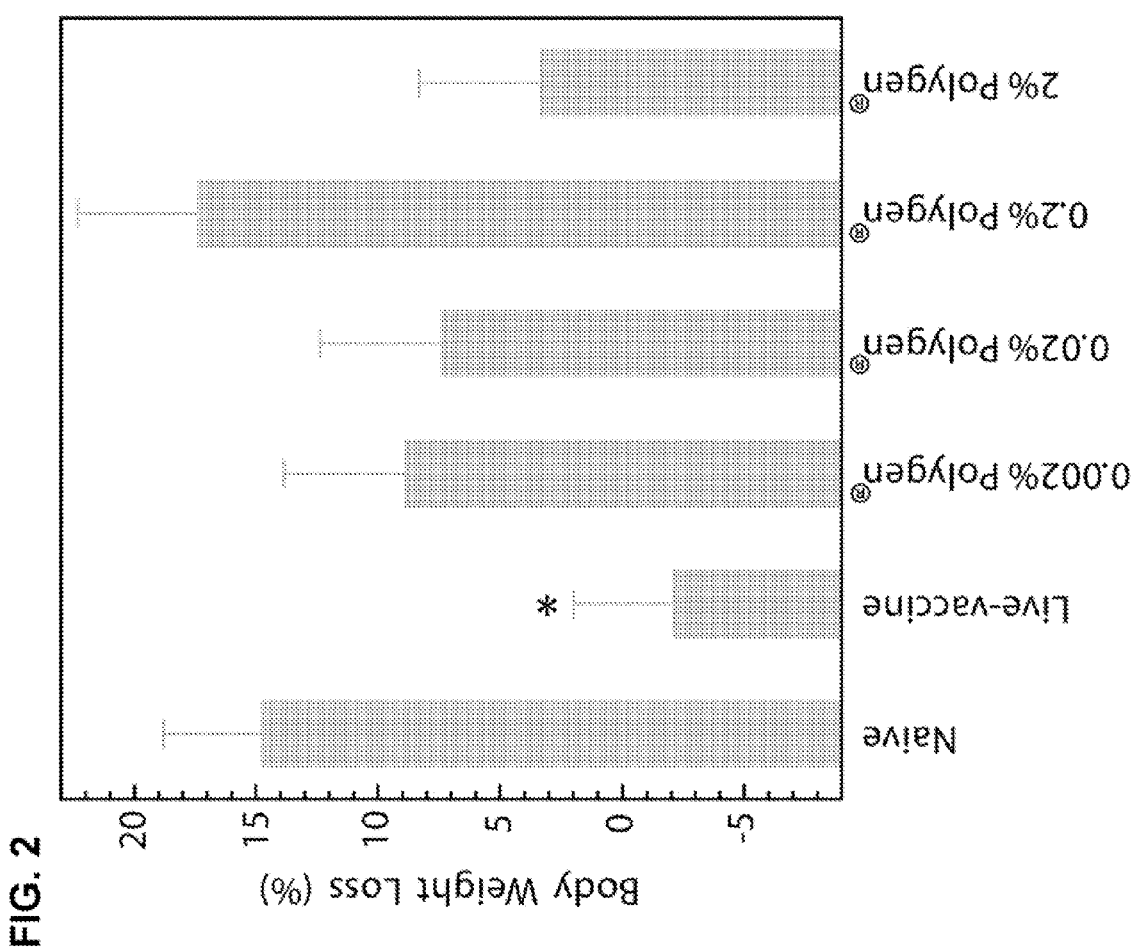
Figure 3:
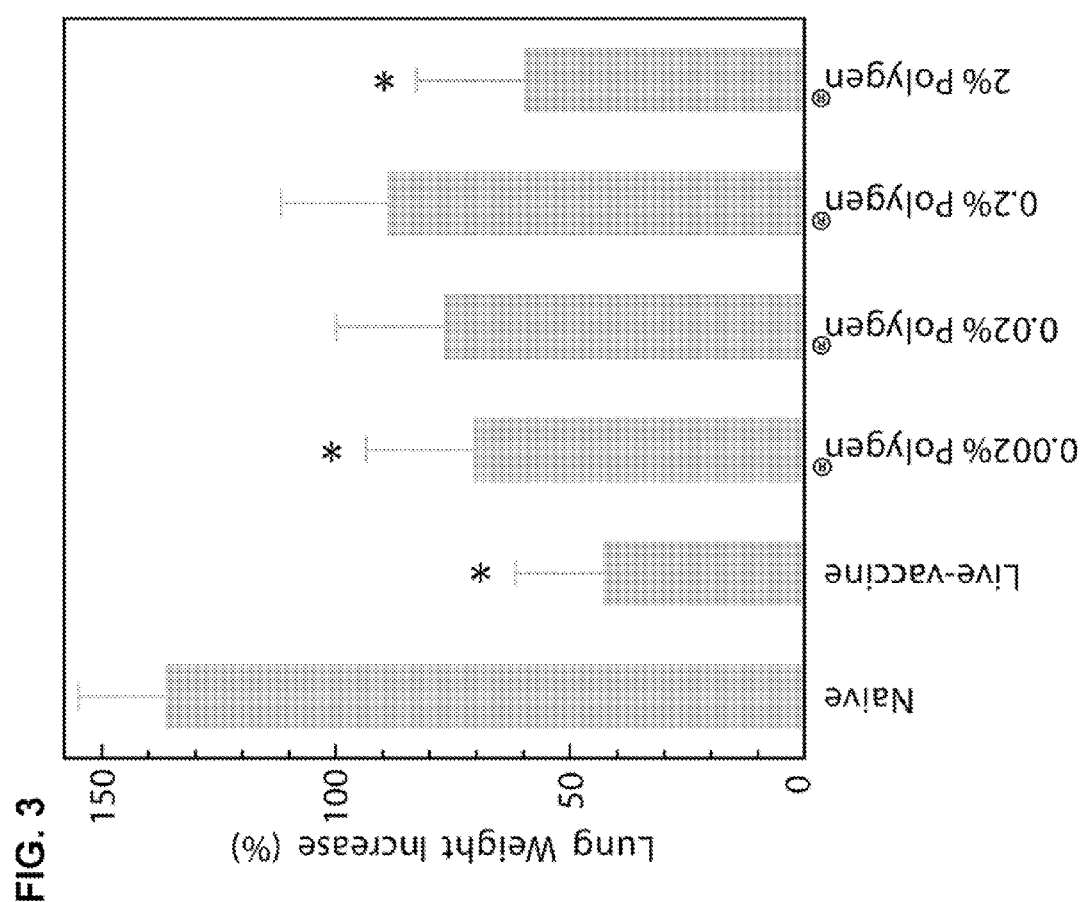
Figure 5:
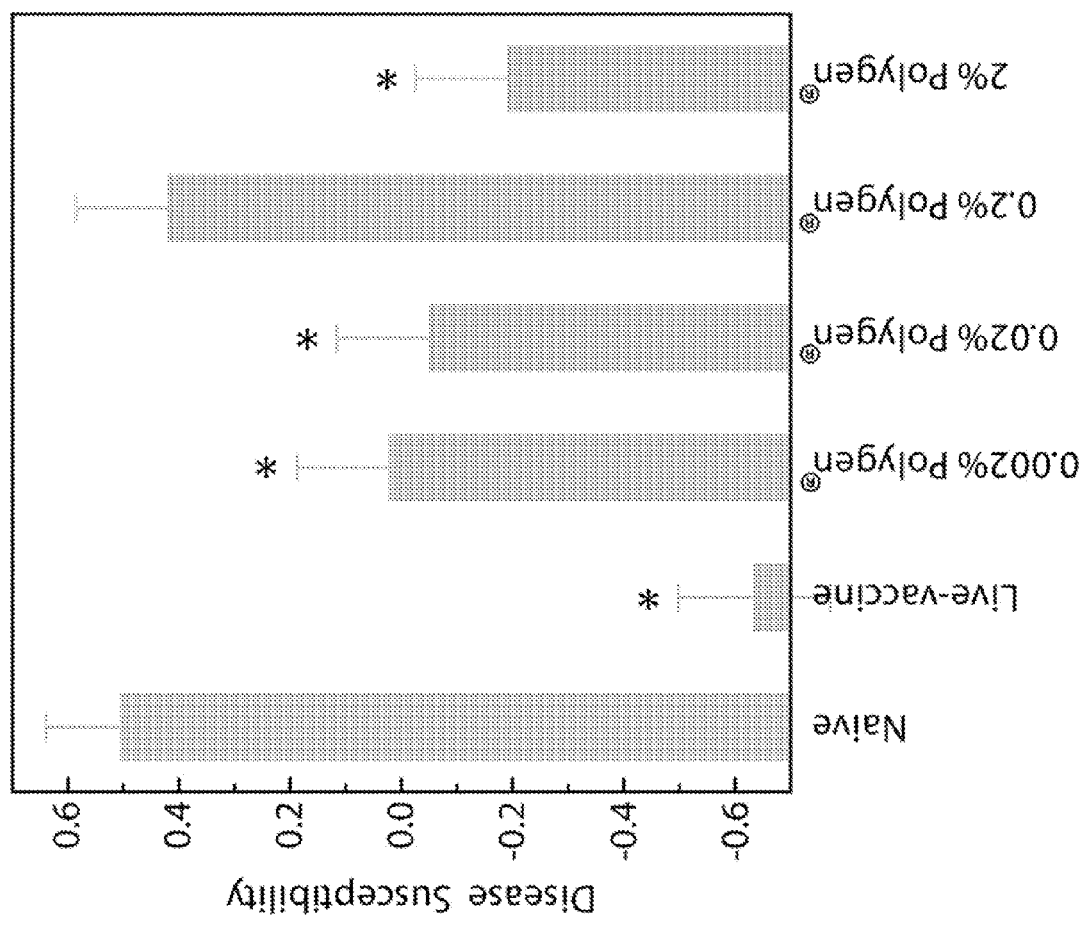

As shown in FIG. 1, vaccination with the low-dose antigen at any dosage of Polygen® adjuvant protects mice against death caused by the *C. abortus* challenge infection, with complete protection from death in the 0.2% and 2% adjuvant groups and the live-vaccine control group. Furthermore, significant reductions in disease as indicated by lung, weight increase were observed in Polygen® adjuvant-vaccinated mice (FIG. 3). Body weight losses (another indicator of disease) and *C. abortus* lung concentration also trended lower in Polygen® adjuvant-vaccinated mice, but did not reach significance (FIGS. 2, 4). In the composite Disease Susceptibility Score, Polygen® adjuvant-vaccinated mice were again significantly protected against disease as compared to the naïve mice (except for the 0.2% outliers; FIG. 5). It should be noted, though, that even the best protected group with 2% Polygen® adjuvant differed significantly from the optimally immunoprotected live-vaccine mice. In the 2% Polygen® adjuvant vaccinated mice, 1 ng of each recombinant protein mediated approximately 61.2% reduction in disease susceptibility from naïve mice as compared to the 100% reduction in live-vaccine mice. In conclusion, there is strong evidence for efficient immune protection against respiratory *C. abortus* challenge mediated by low *C. abortus* vaccine candidate recombinant antigen-dose vaccination.

Example 2

Titration of Overlapping 20-mer Peptide Vaccine

This Example 2 was performed using methods similar to those in Example 1. Three approaches were tested and contrasted against optimum protection by live-vaccination and best vaccine protection by the 2% Polygen® adjuvant—1 ng each recombinant protein antigen vaccine. These included: 1) use of the adjuvant Poly (I:C) at a standard dosage of 50 µg/mouse; 2) use of overlapping 20-mer peptide vaccine antigens derived from the 3 vaccine candidate proteins (DnaX2. GatA, and GatC, and 3) a gradient of peptide quantities. (See Tables 2-4).

TABLE 2

| GROUP | # of female A/J mice | Vaccine | Adjuvant | Week 0 Antigen | Week 4 antigen | Week 8 |
|---|---|---|---|---|---|---|
| 1 C. abortus live-vaccine control | 15 | low-dose infection | — | HBSS | low-dose intranasal C. abortus | C. abortus challenge |
| 2 protein Polygen ® vaccine control | 10 | Proteins | Polygen ® 2% | 1 ng sc | 1 ng sc | C. abortus challenge |
| 3 protein Poly (I:C) vaccine control | 10 | Proteins | Poly (I:C) 50 µg | 1 ng sc | 1 ng sc | C. abortus challenge |
| 4 titer peptide Polygen ® vaccine I | 10 | peptides | Polygen ® 2% | ~1 ng (10 femto M) sc | ~1 ng (10 femto M) sc | C. abortus challenge |
| 5 titer peptide Polygen ® vaccine II | 10 | peptides | Polygen ® 2% | ~0.5 ng (5 femto M) sc | ~0.5 ng (5 femto M) sc | C. abortus challenge |
| 6 titer peptide Polygen ® vaccine III | 10 | peptides | Polygen ® 2% | ~0.25 ng (2.5 femto M) sc | ~0.25 ng (2.5 femto M) sc | C. abortus challenge |
| 7 titer peptide Polygen ® vaccine IV | 10 | peptides | Polygen ® 2% | ~0.1 ng (1 femto M) sc | ~0.1 ng (1 femto M) sc | C. abortus challenge |
| 8 titer peptide Poly (I:C) vaccine I | 10 | peptides | Poly (I:C) 50 µg | ~1 ng (10 femto M) sc | ~1 ng (10 femto M) sc | C. abortus challenge |
| 9 titer peptide Poly (I:C) vaccine II | 10 | peptides | Poly (I:C) 50 µg | ~0.5 ng (5 femto M) sc | ~0.5 ng (5 femto M) sc | C. abortus challenge |
| 10 titer peptide Poly (I:C) vaccine III | 10 | peptides | Poly (I:C) 50 µg | ~0.25 ng (2.5 femto M) sc | ~0.25 ng (2.5 femto M) sc | C. abortus challenge |
| 11 titer peptide Poly (I:C) vaccine IV | 10 | peptides | Poly (I:C) 50 µg | ~0.1 ng (1 femto M) sc | ~0.1 ng (1 femto M) sc | C. abortus challenge |

TABLE 3

*C abortus* DnaX2 (CAB0327)

(SEQ ID NO: 45)

```
MTSATYQVSSRKYRPQTFAEMLGQDAVVTVLKNALQFQRVAHAYLFSGIRGTGKTTLARIFAKALNCKEL
TPEHEPCNQCCVCKEISSGTSLDVIEIDGASHRGIEDIRQINETVLFTPAKSQYKIYIIDEVHMLTKEAF
NSLLKTLEEPPSHVKFFLATTENYKIPSTILSRCQKMHLKRIPETMIVDKLASISQAGGIETSRAELLPI
ARAAQGSLRDAESLYDYVIGLFPTSLSPELVADALGLLSQDTLATLSECIRTQKYAEALLPVTTAINSGV
APITFLHDLTVFYRDVLLNKDQGNSPLSAIAMHYSSECLLEIIDFLGEAAKHLQQTIFEKTFLETVIIHL
IRICQRPSLETLFSQLKTSTFDTVRNVPQQQEPSKPSIQPEKHYQDQSFLTSPSPTPKVQHQKEASPSLV
GSATIDTLLQFAVVEFSGILTKE
```

TABLE 44 overlapping *C. abortus* DnaX2(CAB0327) peptides

| | |
|---|---|
| MTSATYQVSSRKYRPQTFAE | (SEQ ID NO: 1) |
| RKYRPQTFAEMLGQDAVVTV | (SEQ ID NO: 2) |
| MLGQDAVVTVLKNALQFQRV | (SEQ ID NO: 3) |
| LKNALQFQRVAHAYLFSGIR | (SEQ ID NO: 4) |
| AHAYLFSGIRGTGKTTLARI | (SEQ ID NO: 5) |
| GTGKTTLARIFAKALNCKEL | (SEQ ID NO: 6) |
| FAKALNCKELTPEHEPCNQC | (SEQ ID NO: 7) |
| TPEHEPCNQCCVCKEISSGT | (SEQ ID NO: 8) |
| CVCKEISSGTSLDVIEIDGA | (SEQ ID NO: 9) |
| SLDVIEIDGASHRGIEDIRQ | (SEQ ID NO: 10) |
| SHRGIEDIRQINETVLFTPA | (SEQ ID NO: 11) |
| INETVLFTPAKSQYKIYIID | (SEQ ID NO: 12) |
| KSQYKIYIIDEVHMLTKEAF | (SEQ ID NO: 13) |

TABLE 44-continued overlapping *C. abortus* DnaX2(CAB0327) peptides

| | |
|---|---|
| EVHMLTKEAFNSLLKTLEEP | (SEQ ID NO: 14) |
| NSLLKTLEEPPSHVKFFLAT | (SEQ ID NO: 15) |
| PSHVKFFLATTENYKIPSTI | (SEQ ID NO: 16) |
| TENYKIPSTILSRCQKMHLK | (SEQ ID NO: 17) |
| LSRCQKMHLKRIPETMIVDK | (SEQ ID NO: 18) |
| RIPETMIVDKLASISQAGGI | (SEQ ID NO: 19) |
| LASISQAGGIETSREALLPI | (SEQ ID NO: 20) |
| ETSREALLPIARAAQGSLRD | (SEQ ID NO: 21) |
| ARAAQGSLRDAESLYDYVIG | (SEQ ID NO: 22) |
| AESLYDYVIGLFPTSLSPEL | (SEQ ID NO: 23) |
| LFPTSLSPELVADALGLLSQ | (SEQ ID NO: 24) |
| VADALGLLSQDTLATLSECI | (SEQ ID NO: 25) |

TABLE 44-continued overlapping *C. abortus* DnaX2(CAB0327) peptides

| | |
|---|---|
| DTLATLSECIRTQKYAEALL | (SEQ ID NO: 26) |
| RTQKYAEALLPVTTAINSGV | (SEQ ID NO: 27) |
| PVTTAINSGVAPITFLHDLT | (SEQ ID NO: 28) |
| APITFLHDLTVFYRDVLLNK | (SEQ ID NO: 29) |
| VFYRDVLLNKDQGNSPLSAI | (SEQ ID NO: 30) |
| DQGNSPLDAISMHYSSECLL | (SEQ ID NO: 31) |
| AMHYSSECLLEIIDFLGEAA | (SEQ ID NO: 32) |
| EIIDFLGEAAKHLQQTIFEK | (SEQ ID NO: 33) |
| KHLQQTIFEKTFLETVIIHL | (SEQ ID NO: 34) |
| TFLETVIIHLIRICQRPSLE | (SEQ ID NO: 35) |
| IRICQRPSLETLFSQLKTST | (SEQ ID NO: 36) |
| TLFSQLKTSTFDTVRNVPQQ | (SEQ ID NO: 37) |
| FDTVRNVPQQQEPSKPSIQP | (SEQ ID NO: 38) |
| QEPSKPSIQPEKHYQDQSFL | (SEQ ID NO: 39) |
| EKHYQDQSFLTSPSPTPKVQ | (SEQ ID NO: 40) |
| TSPSPTPKVQHQKEASPSLV | (SEQ ID NO: 41) |
| HQKEASPSLVGSATIDTLLQ | (SEQ ID NO: 42) |
| GSATIDTLLQFAVVEFSGIL | (SEQ ID NO: 43) |
| FAVVEFSGILTKE | (SEQ ID NO: 44) |

The experimental conditions of the mouse *C. abortus* challenge model in Example 2 were identical to those of Example 1 Poly (I:C) was used at 50 µg per vaccine dose of 200 µl. The peptides used were 20-mer peptides completely encompassing the amino acid sequence of each of DnaX2, GatA, and GatC. The amino acid sequence of each protein was broken up into 20-mers that each overlapped by 10 amino acids with the previous peptide. For example DnaX2 has a molecular weight of 49,183 Daltons and is composed of 443 amino acids. DnaX2 was broken up into peptides according to the approach described above. (See FIG. 6 and Tables 3, 4) One nanogram of the protein corresponds to approximately 20 femtoMoles. The one nanogram equivalent of all peptides consisted therefore of 10 femtoMoles of each peptide (i.e., the complete sequence is coded twice by adjacent, non-overlapping 20-mer peptides). Because the average molecular weight of each peptide is approximately 2,200 Daltons, the average amount of the 10 femtoMoles of each peptide is 22 picograms.

Figure 7:
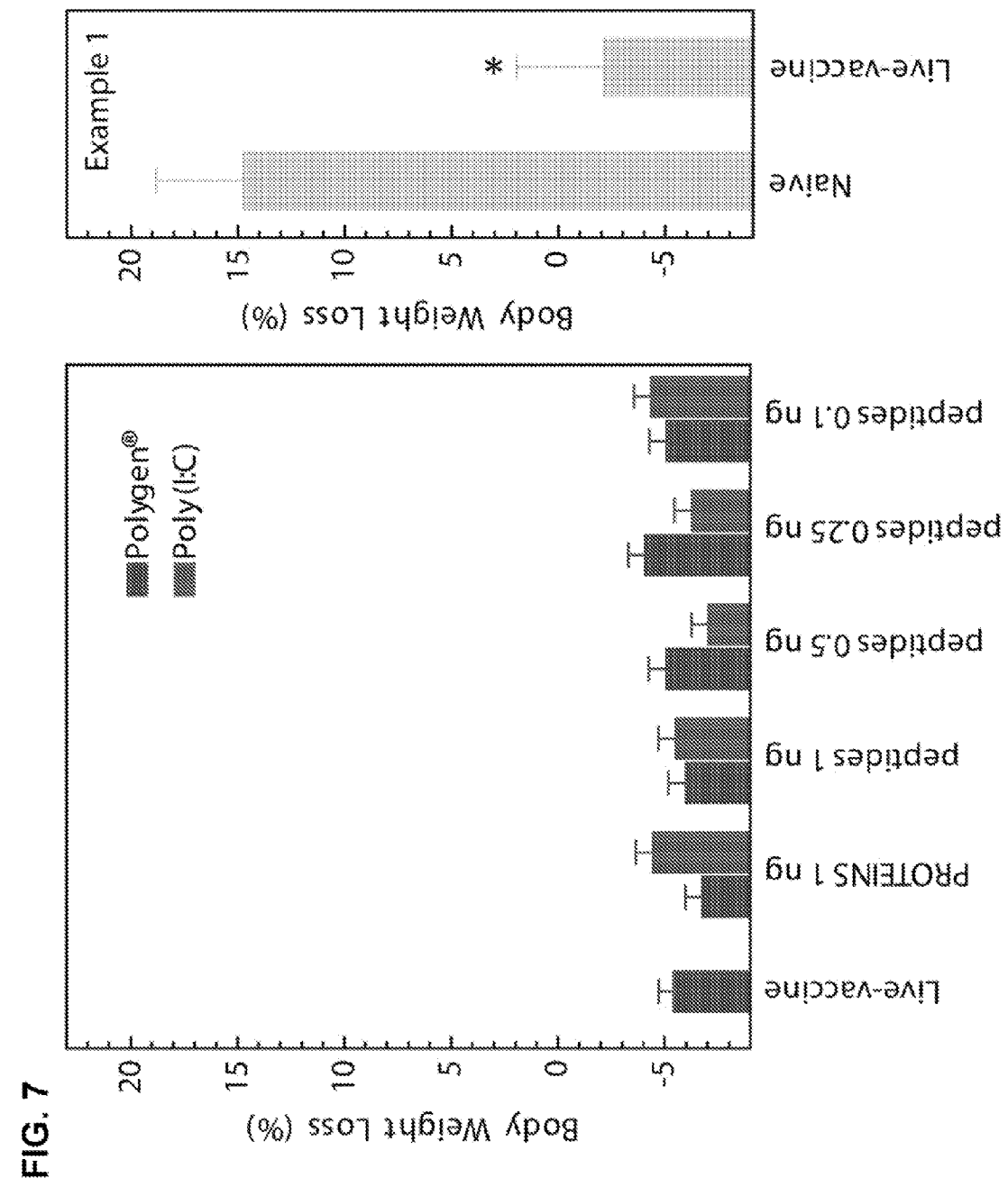
Figure 8:
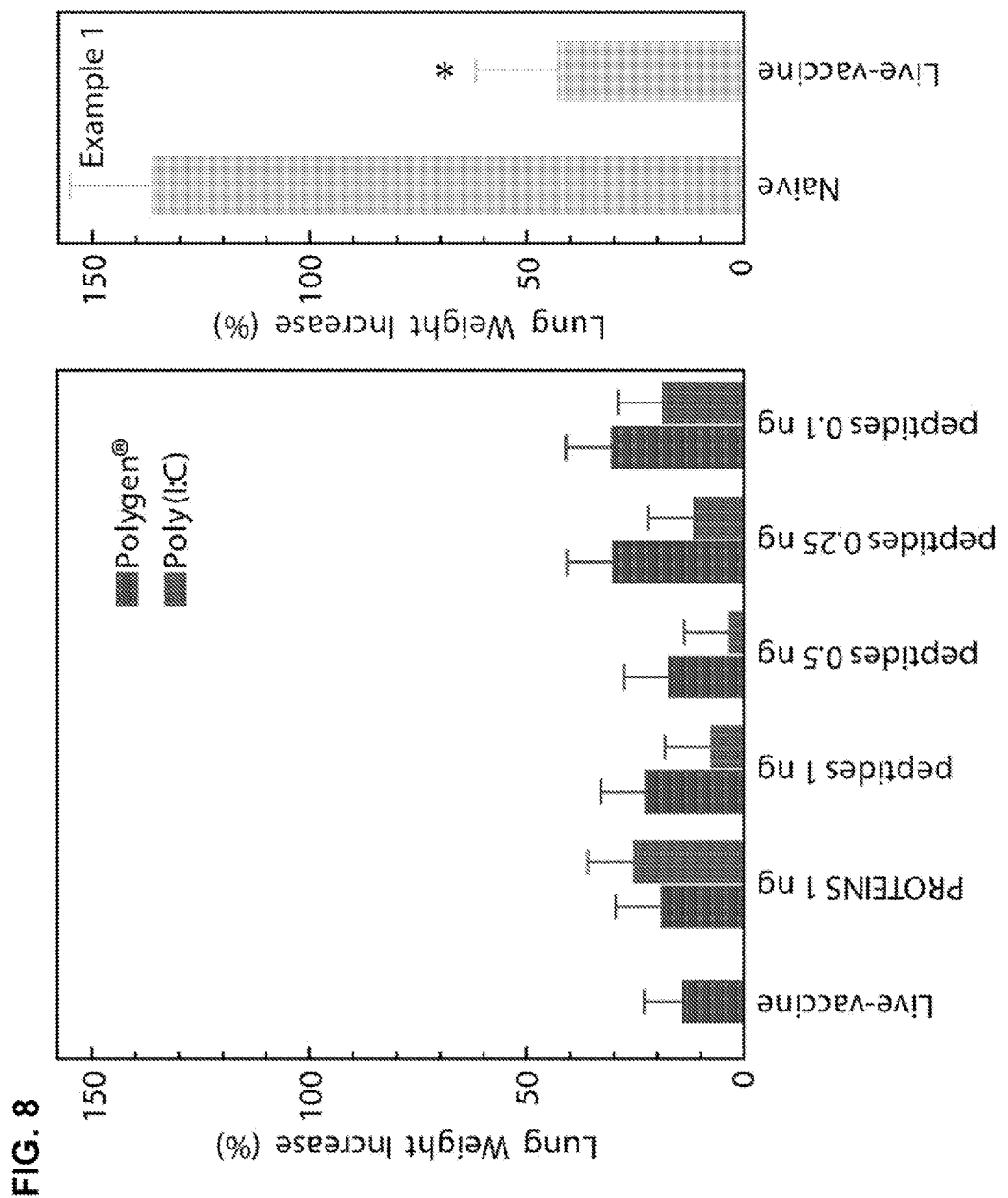
Figure 9:
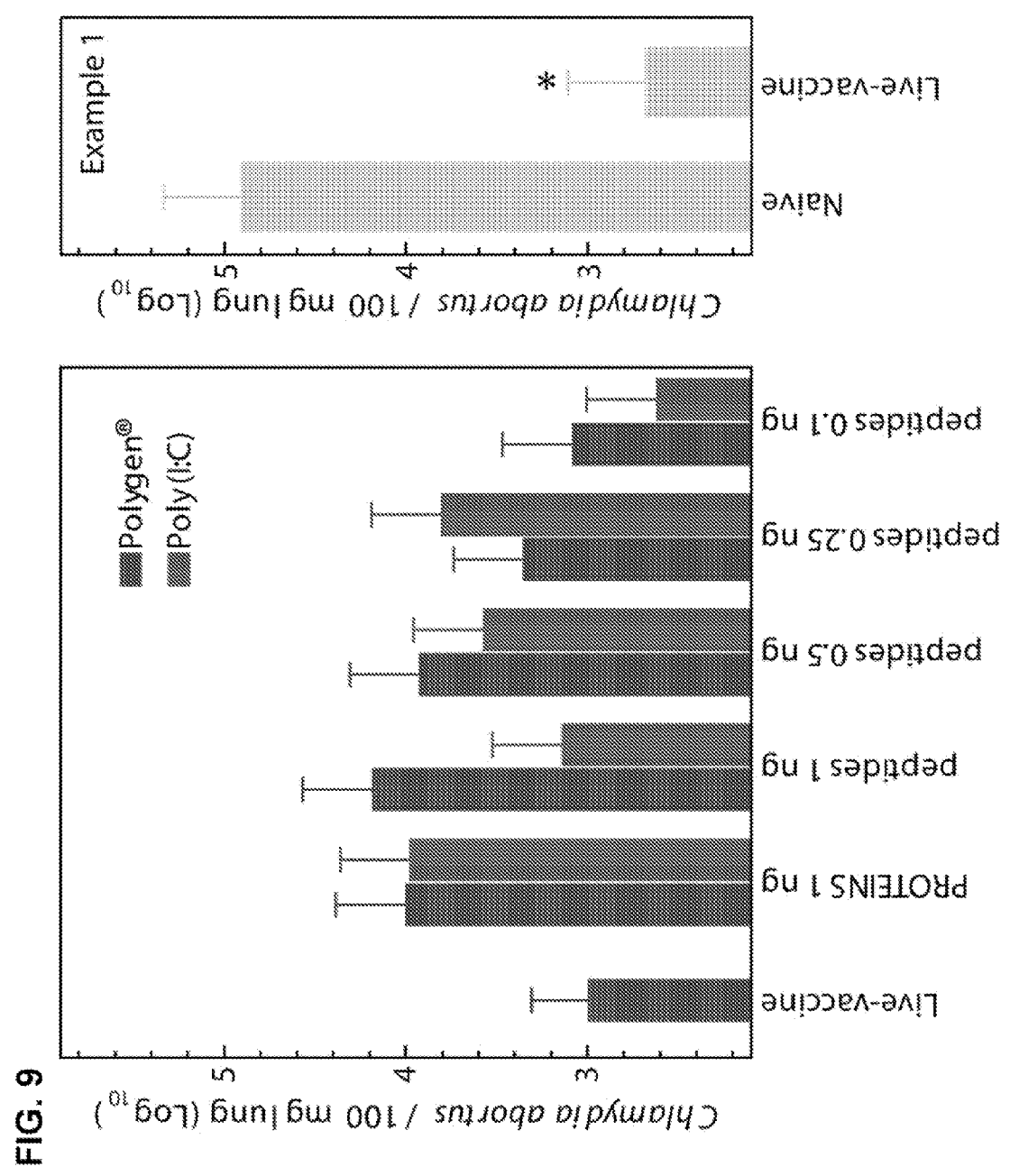
Figure 10:
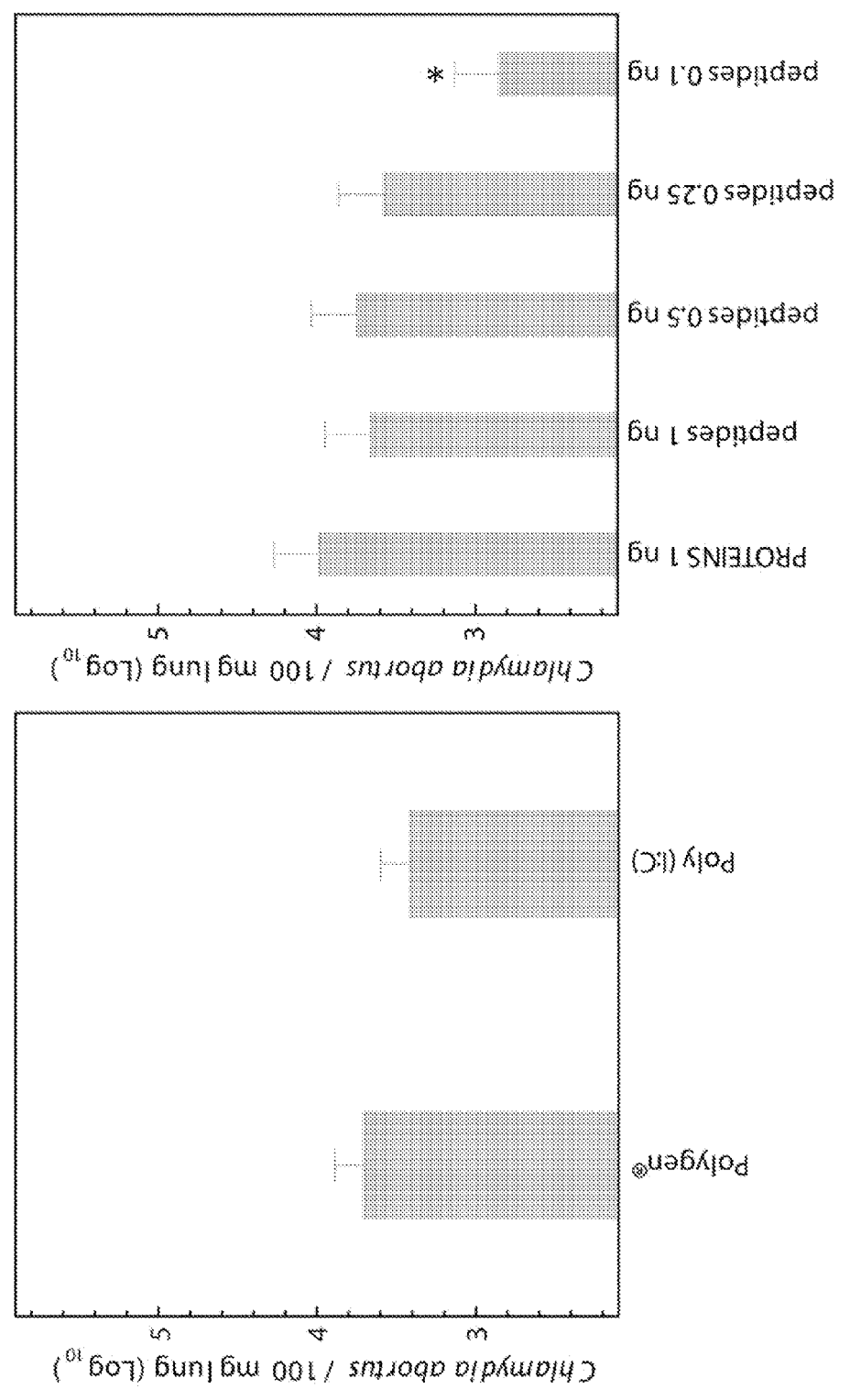
Figure 11:
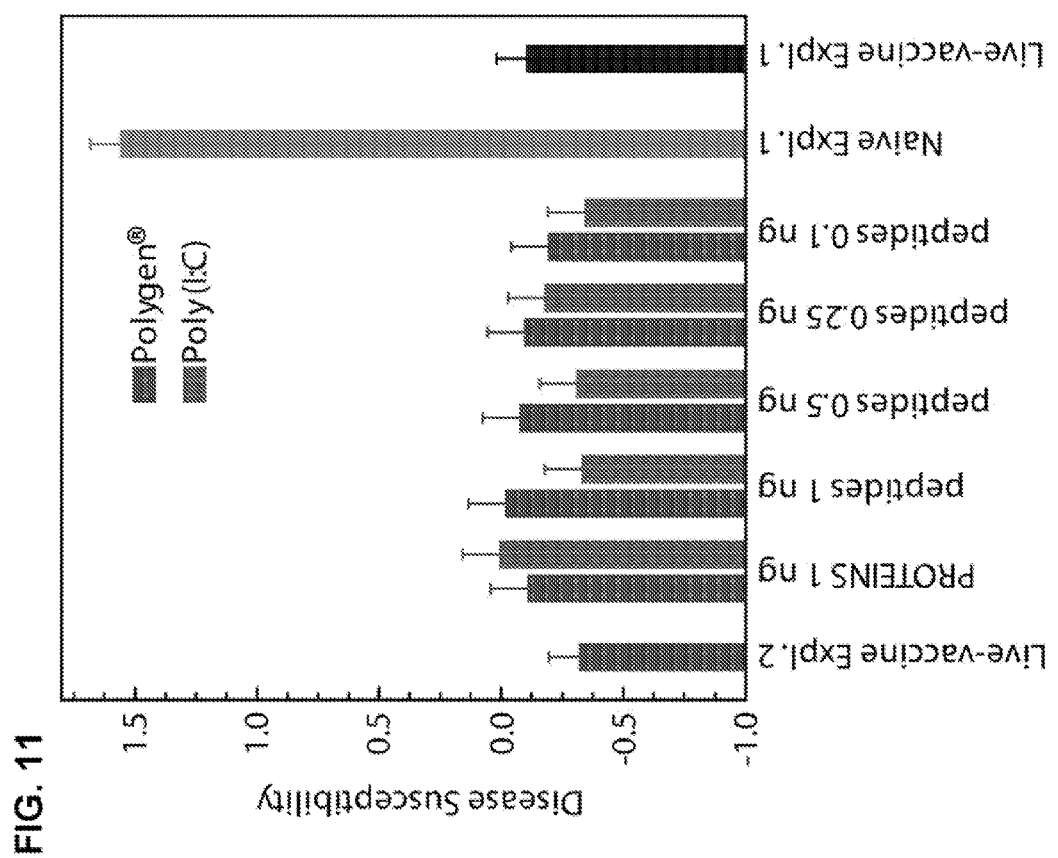

As in Example 1, vaccination completely protected mice from disease and death induced by the *C. abortus* challenge infection. In contrast to Example 1, however, in both disease-indicating parameters none of the vaccine groups was statistically different from the live-vaccine control (FIGS. 7, 8). Thus, by this measure alone all vaccine compositions were more effective than those in Example 1. *C. abortus* lung concentrations in the groups vaccinated with Polygen® adjuvant-vaccinated mice and 1 ng of proteins or peptides were significantly higher than in the live-vaccine controls, but not in the groups vaccinated with lower amounts of peptides or with Poly (I:C) adjuvant (FIG. 9). Dissection of the effectors in FIG. 10 demonstrates that lower peptide amounts, significantly 0.1 ng of peptides, associate with lower *C. abortus* lung loads while adjuvants do not significantly differ in their influence on chlamydial loads. In the composite Disease Susceptibility Score calibrated against disease susceptibility of naïve and live-vaccine controls in Example 1, none of the vaccine groups were significantly different from the live-vaccine controls of Example 2 (FIG. 11). The data indicate that protein vaccines mediate less than 100% protection relative to the live-vaccine controls in Example 2. In contrast, peptide vaccines, particularly combined with Poly (I:C) adjuvant at 1, 0.5, and 0.1 ng peptide doses mediate essentially 100% protection.

Thus, in conclusion the results of Example 2 indicate: 1) that different adjuvants mediate the induction of protective immunity against *C. abortus* in low antigen-dose vaccination; 2) that overlapping synthetic peptides of the protective proteins mediate protection as efficiently as the corresponding whole proteins; and 3) that further reduced doses of the peptides as compared to the 1 ng protein dose mediate better immunoprotection by enhancing chlamydial elimination. In summary, overlapping 20-mer peptide antigens at amounts as low as 0.1 ng in total combined with adjuvant mediate essentially 100% protection as compared to live-vaccine controls.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for inducing in a subject in need thereof a protective T-cell immune response against a disease, the method comprising administering a vaccine comprising one or more antigens to the subject wherein the vaccine is administered at a dose that delivers no more than 2 pg each antigen per 1 g body weight of the subject, wherein the one or more antigens comprise a panel of peptides and the panel comprises one or more peptides having an amino acid sequence that overlaps at least one other peptide of the panel.

2. The method of claim 1, wherein the vaccine is administered at a dose that delivers no more than 1 pg antigen per 1 g body weight of the subject.

3. The method of claim 1, wherein the vaccine is administered at a dose that delivers no more than 0.5 pg antigen per 1 g body weight of the subject.

4. The method of claim 1, wherein the vaccine is administered at a dose that delivers no more than 0.1 pg antigen per 1 g body weight of the subject.

5. The method of claim 1, wherein the vaccine is administered at a dose that delivers no more than 0.05 pg antigen per 1 g body weight of the subject.

6. The method of claim 1, wherein the vaccine is administered at a dose that delivers no more than 0.01 pg antigen per 1 g body weight of the subject.

7. The method of claim 1, wherein the method comprises administering the vaccine, waiting for at least about 4 weeks, and then administering the vaccine again.

8. The method of claim 1, wherein the method induces an immune response against a pathogen.

9. The method of claim 8, wherein the pathogen is a bacteria.

10. The method of claim 9, wherein the bacteria is a member of *Chlamydia* spp.

11. The method of claim 10, wherein the bacteria is *Chlamydia abortus, Chlamydia trachomitis, Chlamydia suis, Chlamydia muridarum, Chlamydophila pneumoniae, Chlamydophila pecorum, Chlamydophila psittaci, Chlamydophila abortus, Chlamydophila felis,* and *Chlamydophila caviae.*

12. The method of claim 1, wherein each peptide of the panel has an amino acid sequence of 5-200 amino acids.

13. The method of claim 1, wherein one or more of the peptides in the panel has an amino acid sequence that overlaps by 5-10 amino acids with at least one other peptide of the panel.

14. The method of claim 1, wherein each peptide of the panel has an amino acid sequence that overlaps by 5-10 amino acids with another at least one other peptide of the panel.

15. The method of claim 12, wherein the vaccine is administered at a dose that delivers no more than 1 femtomole each peptide per 1 g body weight of the subject.

16. The method of claim 1, wherein the method induces an immune response against a disease and the peptides of the panel have an amino acid sequence of 10-20 amino acids corresponding to an amino acid sequence of a protein associated with the disease, and one or more of the peptides in the panel has an amino acid sequence that overlaps by 5-10 amino acids with at least one other peptide of the panel.

17. The method of claim 16, wherein each peptide has an amino acid sequence that overlaps by 5-10 amino acids with at least one other peptide of the panel.

18. The method of claim 1, wherein the subject is a human.

19. The method of claim 1, wherein the subject is a bovine, a porcine, a canine, or a feline.

20. The method of claim 1, wherein the vaccine further comprises a pharmaceutical solution comprising a carrier, diluent, excipient, or adjuvant.

* * * * *

SEQUENCE LISTING

<160> NUMBER OF SEQ ID NOS: 45

<210> SEQ ID NO 1

-continued

```
<211> LENGTH: 20
<212> TYPE: PRT
<213> ORGANISM: Chlamydophila abortus

<400> SEQUENCE: 1

Met Thr Ser Ala Thr Tyr Gln Val Ser Ser Arg Lys Tyr Arg Pro Gln
1               5                   10                  15

Thr Phe Ala Glu
            20

<210> SEQ ID NO 2
<211> LENGTH: 20
<212> TYPE: PRT
<213> ORGANISM: Chlamydophila abortus

<400> SEQUENCE: 2

Arg Lys Tyr Arg Pro Gln Thr Phe Ala Glu Met Leu Gly Gln Asp Ala
1               5                   10                  15

Val Val Thr Val
            20

<210> SEQ ID NO 3
<211> LENGTH: 20
<212> TYPE: PRT
<213> ORGANISM: Chlamydophila abortus

<400> SEQUENCE: 3

Met Leu Gly Gln Asp Ala Val Val Thr Val Leu Lys Asn Ala Leu Gln
1               5                   10                  15

Phe Gln Arg Val
            20

<210> SEQ ID NO 4
<211> LENGTH: 20
<212> TYPE: PRT
<213> ORGANISM: Chlamydophila abortus

<400> SEQUENCE: 4

Leu Lys Asn Ala Leu Gln Phe Gln Arg Val Ala His Ala Tyr Leu Phe
1               5                   10                  15

Ser Gly Ile Arg
            20

<210> SEQ ID NO 5
<211> LENGTH: 20
<212> TYPE: PRT
<213> ORGANISM: Chlamydophila abortus

<400> SEQUENCE: 5

Ala His Ala Tyr Leu Phe Ser Gly Ile Arg Gly Thr Gly Lys Thr Thr
1               5                   10                  15

Leu Ala Arg Ile
            20

<210> SEQ ID NO 6
<211> LENGTH: 20
<212> TYPE: PRT
<213> ORGANISM: Chlamydophila abortus

<400> SEQUENCE: 6

Gly Thr Gly Lys Thr Thr Leu Ala Arg Ile Phe Ala Lys Ala Leu Asn
1               5                   10                  15

Cys Lys Glu Leu
```

```
                                           20

<210> SEQ ID NO 7
<211> LENGTH: 20
<212> TYPE: PRT
<213> ORGANISM: Chlamydophila abortus

<400> SEQUENCE: 7

Phe Ala Lys Ala Leu Asn Cys Lys Glu Leu Thr Pro Glu His Glu Pro
1               5                   10                  15

Cys Asn Gln Cys
            20

<210> SEQ ID NO 8
<211> LENGTH: 20
<212> TYPE: PRT
<213> ORGANISM: Chlamydophila abortus

<400> SEQUENCE: 8

Thr Pro Glu His Glu Pro Cys Asn Gln Cys Cys Val Cys Lys Glu Ile
1               5                   10                  15

Ser Ser Gly Thr
            20

<210> SEQ ID NO 9
<211> LENGTH: 20
<212> TYPE: PRT
<213> ORGANISM: Chlamydophila abortus

<400> SEQUENCE: 9

Cys Val Cys Lys Glu Ile Ser Ser Gly Thr Ser Leu Asp Val Ile Glu
1               5                   10                  15

Ile Asp Gly Ala
            20

<210> SEQ ID NO 10
<211> LENGTH: 20
<212> TYPE: PRT
<213> ORGANISM: Chlamydophila abortus

<400> SEQUENCE: 10

Ser Leu Asp Val Ile Glu Ile Asp Gly Ala Ser His Arg Gly Ile Glu
1               5                   10                  15

Asp Ile Arg Gln
            20

<210> SEQ ID NO 11
<211> LENGTH: 20
<212> TYPE: PRT
<213> ORGANISM: Chlamydophila abortus

<400> SEQUENCE: 11

Ser His Arg Gly Ile Glu Asp Ile Arg Gln Ile Asn Glu Thr Val Leu
1               5                   10                  15

Phe Thr Pro Ala
            20

<210> SEQ ID NO 12
<211> LENGTH: 20
<212> TYPE: PRT
<213> ORGANISM: Chlamydophila abortus

<400> SEQUENCE: 12
```

```
Ile Asn Glu Thr Val Leu Phe Thr Pro Ala Lys Ser Gln Tyr Lys Ile
1               5                   10                  15

Tyr Ile Ile Asp
            20
```

<210> SEQ ID NO 13
<211> LENGTH: 20
<212> TYPE: PRT
<213> ORGANISM: Chlamydophila abortus

<400> SEQUENCE: 13

```
Lys Ser Gln Tyr Lys Ile Tyr Ile Ile Asp Glu Val His Met Leu Thr
1               5                   10                  15

Lys Glu Ala Phe
            20
```

<210> SEQ ID NO 14
<211> LENGTH: 20
<212> TYPE: PRT
<213> ORGANISM: Chlamydophila abortus

<400> SEQUENCE: 14

```
Glu Val His Met Leu Thr Lys Glu Ala Phe Asn Ser Leu Leu Lys Thr
1               5                   10                  15

Leu Glu Glu Pro
            20
```

<210> SEQ ID NO 15
<211> LENGTH: 20
<212> TYPE: PRT
<213> ORGANISM: Chlamydophila abortus

<400> SEQUENCE: 15

```
Asn Ser Leu Leu Lys Thr Leu Glu Glu Pro Pro Ser His Val Lys Phe
1               5                   10                  15

Phe Leu Ala Thr
            20
```

<210> SEQ ID NO 16
<211> LENGTH: 20
<212> TYPE: PRT
<213> ORGANISM: Chlamydophila abortus

<400> SEQUENCE: 16

```
Pro Ser His Val Lys Phe Phe Leu Ala Thr Thr Glu Asn Tyr Lys Ile
1               5                   10                  15

Pro Ser Thr Ile
            20
```

<210> SEQ ID NO 17
<211> LENGTH: 20
<212> TYPE: PRT
<213> ORGANISM: Chlamydophila abortus

<400> SEQUENCE: 17

```
Thr Glu Asn Tyr Lys Ile Pro Ser Thr Ile Leu Ser Arg Cys Gln Lys
1               5                   10                  15

Met His Leu Lys
            20
```

<210> SEQ ID NO 18
<211> LENGTH: 20
<212> TYPE: PRT

<213> ORGANISM: Chlamydophila abortus

<400> SEQUENCE: 18

```
Leu Ser Arg Cys Gln Lys Met His Leu Lys Arg Ile Pro Glu Thr Met
1               5                   10                  15

Ile Val Asp Lys
            20
```

<210> SEQ ID NO 19
<211> LENGTH: 20
<212> TYPE: PRT
<213> ORGANISM: Chlamydophila abortus

<400> SEQUENCE: 19

```
Arg Ile Pro Glu Thr Met Ile Val Asp Lys Leu Ala Ser Ile Ser Gln
1               5                   10                  15

Ala Gly Gly Ile
            20
```

<210> SEQ ID NO 20
<211> LENGTH: 20
<212> TYPE: PRT
<213> ORGANISM: Chlamydophila abortus

<400> SEQUENCE: 20

```
Leu Ala Ser Ile Ser Gln Ala Gly Gly Ile Glu Thr Ser Arg Glu Ala
1               5                   10                  15

Leu Leu Pro Ile
            20
```

<210> SEQ ID NO 21
<211> LENGTH: 20
<212> TYPE: PRT
<213> ORGANISM: Chlamydophila abortus

<400> SEQUENCE: 21

```
Glu Thr Ser Arg Glu Ala Leu Leu Pro Ile Ala Arg Ala Ala Gln Gly
1               5                   10                  15

Ser Leu Arg Asp
            20
```

<210> SEQ ID NO 22
<211> LENGTH: 20
<212> TYPE: PRT
<213> ORGANISM: Chlamydophila abortus

<400> SEQUENCE: 22

```
Ala Arg Ala Ala Gln Gly Ser Leu Arg Asp Ala Glu Ser Leu Tyr Asp
1               5                   10                  15

Tyr Val Ile Gly
            20
```

<210> SEQ ID NO 23
<211> LENGTH: 20
<212> TYPE: PRT
<213> ORGANISM: Chlamydophila abortus

<400> SEQUENCE: 23

```
Ala Glu Ser Leu Tyr Asp Tyr Val Ile Gly Leu Phe Pro Thr Ser Leu
1               5                   10                  15

Ser Pro Glu Leu
            20
```

```
<210> SEQ ID NO 24
<211> LENGTH: 20
<212> TYPE: PRT
<213> ORGANISM: Chlamydophila abortus

<400> SEQUENCE: 24

Leu Phe Pro Th

```
Leu Leu Asn Lys
            20

<210> SEQ ID NO 30
<211> LENGTH: 20
<212> TYPE: PRT
<213> ORGANISM: Chlamydophila abortus

<400> SEQUENCE: 30

Val Phe Tyr Arg Asp Val Leu Leu Asn Lys Asp Gln Gly Asn Ser Pro
1               5                   10                  15

Leu Ser Ala Ile
            20

<210> SEQ ID NO 31
<211> LENGTH: 20
<212> TYPE: PRT
<213> ORGANISM: Chlamydophila abortus

<400> SEQUENCE: 31

Asp Gln Gly Asn Ser Pro Leu Ser

-continued

```
<400> SEQUENCE: 35

Thr Phe Leu Glu Thr Val Ile Ile His Leu Ile Arg Ile Cys Gln Arg
1               5                   10                  15

Pro Ser Leu Glu
            20

<210> SEQ ID NO 36
<211> LENGTH: 20
<212> TYPE: PRT
<213> ORGANISM: Chlamydophila abortus

<400> SEQUENCE: 36

Ile Arg Ile Cys Gln Arg Pro Ser Leu Glu Thr Leu Phe Ser Gln Leu
1               5                   10                  15

Lys Thr Ser Thr
            20

<210> SEQ ID NO 37
<211> LENGTH: 20
<212> TYPE: PRT
<213> ORGANISM: Chlamydophila abortus

<400> SEQUENCE: 37

Thr Leu Phe Ser Gln Leu Lys Thr Ser Thr Phe Asp Thr Val Arg Asn
1               5                   10                  15

Val Pro Gln Gln
            20

-continued

```
<211> LENGTH: 20
<212> TYPE: PRT
<213> ORGANISM: Chlamydophila abortus

<400> SE

-continued

```
Glu Thr Val Leu Phe Thr Pro Ala Lys Ser Gln Tyr Lys Ile Tyr Ile
        115                 120                 125

Ile Asp Glu Val His Met Leu Thr Lys Glu Ala Phe Asn Ser Leu Leu
    130                 135                 140

Lys Thr Leu Glu Glu Pro Pro Ser His Val Lys Phe Phe Leu Ala Thr
145                 150                 155                 160

Thr Glu Asn Tyr Lys Ile Pro Ser Thr Ile Leu Ser Arg Cys Gln Lys
                165                 170                 175

Met His Leu Lys Arg Ile Pro Glu Thr Met Ile Val Asp Lys Leu Ala
            180                 185                 190

Ser Ile Ser Gln Ala Gly Gly Ile Glu Thr Ser Arg Glu Ala Leu Leu
        195                 200                 205

Pro Ile Ala Arg Ala Ala Gln Gly Ser Leu Arg Asp Ala Glu Ser Leu
    210                 215                 220

Tyr Asp Tyr Val Ile Gly Leu Phe Pro Thr Ser Leu Ser Pro Glu Leu
225                 230                 235                 240

Val Ala Asp Ala Leu Gly Leu Leu Ser Gln Asp Thr Leu Ala Thr Leu
                245                 250                 255

Ser Glu Cys Ile Arg Thr Gln Lys Tyr Ala Glu Ala Leu Leu Pro Val
            260                 265                 270

Thr Thr Ala Ile Asn Ser Gly Val Ala Pro Ile Thr Phe Leu His Asp
        275                 280                 285

Leu Thr Val Phe Tyr Arg Asp Val Leu Leu Asn Lys Asp Gln Gly Asn
    290                 295                 300

Ser Pro Leu Ser Ala Ile Ala Met His Tyr Ser Ser Glu Cys Leu Leu
305                 310                 315                 320

Glu Ile Ile Asp Phe Leu Gly Glu Ala Ala Lys His Leu Gln Gln Thr
                325                 330                 335

Ile Phe Glu Lys Thr Phe Leu Glu Thr Val Ile Ile His Leu Ile Arg
            340                 345                 350

Ile Cys Gln Arg Pro Ser Leu Glu Thr Leu Phe Ser Gln Leu Lys Thr
        355                 360                 365

Ser Thr Phe Asp Thr Val Arg Asn Val Pro Gln Gln Gln Glu Pro Ser
    370                 375                 380

Lys Pro Ser Ile Gln Pro Glu Lys His Tyr Gln Asp Gln Ser Phe Leu
385                 390                 395                 400

Thr Ser Pro Ser Pro Thr Pro Lys Val Gln His Gln Lys Glu Ala Ser
                405                 410                 415

Pro Ser Leu Val Gly Ser Ala Thr Ile Asp Thr Leu Leu Gln Phe Ala
            420                 425                 430

Val Val Glu Phe Ser Gly Ile Leu Thr Lys Glu
        435                 440
```